United States Patent [19]
Borzatta et al.

[11] Patent Number: 6,046,304
[45] Date of Patent: Apr. 4, 2000

[54] BLOCK OLIGOMERS CONTAINING 2,2,6,6-TETRAMETHYL-4-PIPERIDYL GROUPS AS STABILIZERS FOR ORGANIC MATERIALS

[75] Inventors: Valerio Borzatta; Fabrizio Guizzardi, both of Bologna, Italy

[73] Assignee: Ciba Specialty Chemicals Corporation, Tarrytown, N.Y.

[21] Appl. No.: 08/756,225

[22] Filed: Nov. 25, 1996

[30] Foreign Application Priority Data

| Dec. 4, 1995 | [EP] | European Pat. Off. | 95810756 |
| Jan. 29, 1996 | [EP] | European Pat. Off. | 96810053 |
| Jul. 12, 1996 | [EP] | European Pat. Off. | 96810458 |

[51] Int. Cl.⁷ ...................... C07D 403/00; C07D 403/12
[52] U.S. Cl. .......................... 528/423; 544/191; 544/204; 544/209
[58] Field of Search ............................ 528/423; 544/191, 544/204, 209

[56] References Cited

U.S. PATENT DOCUMENTS

| 4,086,204 | 4/1978 | Cassandrini et al. . |
| 4,108,829 | 8/1978 | Cassandrini et al. . |
| 4,234,707 | 11/1980 | Rody et al. . |
| 4,316,837 | 2/1982 | Molt et al. . |
| 4,331,586 | 5/1982 | Hardy . |
| 4,335,242 | 6/1982 | Wiezor et al. . |
| 4,442,250 | 4/1984 | Cantatore . |
| 4,492,791 | 1/1985 | Orban et al. . |
| 4,743,688 | 5/1988 | Minagawa et al. . |
| 4,789,706 | 12/1988 | Williams . |
| 5,171,855 | 12/1992 | Borzatta et al. ........................ 544/212 |
| 5,198,546 | 3/1993 | Borzatta et al. ........................ 544/198 |
| 5,208,385 | 5/1993 | Kohn et al. . |
| 5,324,834 | 6/1994 | Borzatta et al. ........................ 544/198 |
| 5,449,776 | 9/1995 | Vignali et al. ........................... 544/198 |
| 5,603,885 | 2/1997 | McGinty ................................ 264/205 |
| 5,840,954 | 11/1998 | Quotschalla et al. ..................... 558/71 |

FOREIGN PATENT DOCUMENTS

| 0093693 | 4/1983 | European Pat. Off. . |
| 0117229 | 1/1984 | European Pat. Off. . |
| 0357223 | 7/1989 | European Pat. Off. . |
| 0377324 | 12/1989 | European Pat. Off. . |
| 0446171 | 9/1991 | European Pat. Off. . |
| 0592363 | 4/1994 | European Pat. Off. . |
| 0659750 | 6/1995 | European Pat. Off. . |
| 9521157 | 2/1994 | WIPO . |

OTHER PUBLICATIONS

Chemical Abstracts, vol. 102, 1985.
Derwent Abstract No. 84–214929/35 Cilia Feb. 4, 1983.
Derwent Abst 91–269006/37.
Derwent Abst 94–120444/15.
Data sheet for CHIMASSORB® 944 from Ciba Specialty Chemicals Corporation.

*Primary Examiner*—Jeffrey C. Mullis
*Attorney, Agent, or Firm*—Luther A. R. Hall; Jacob M. Levine

[57] ABSTRACT

Compounds of the formula (I)

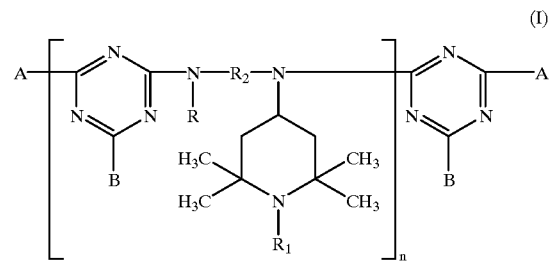

in which the polydispersity $\bar{M}w/\bar{M}n$ is 1; n is 3, 4, 5, 6, 7, 8, 9, 10, 11, 12, 13, 14 or 15; the radicals $R_1$ are for example hydrogen or $C_1$–$C_8$alkyl; $R_2$ is for example $C_2$–$C_{12}$alkylene; the radicals A are independently of one another —$OR_3$, —$N(R_4)(R_5)$ or a group of the formula

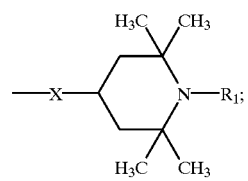

$R_3$, $R_4$ and $R_5$, which are identical or different, are for example hydrogen or $C_1$–$C_{18}$alkyl,
or —$N(R_4)(R_5)$ is additionally a group of the formula

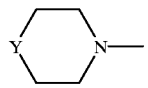

with Y being —O—, —$CH_2$—, —$CH_2CH_2$— or >N—$CH_3$; X is —O— or >N—$R_6$; $R_6$ is for example hydrogen or $C_1$–$C_{18}$alkyl; R is preferably a group of the formula

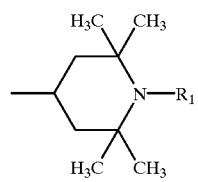

and the radicals B have independently of one another one of the definitions given for A; with the proviso that in the individual recurrent units of the formula (I), each of the radicals B, R, $R_1$ and $R_2$ has the same or a different meaning.

The indicated compounds are useful as light stabilizers, heat stabilizers and oxidation stabilizers for organic materials, in particular synthetic polymers.

28 Claims, 15 Drawing Sheets

EXAMPLE 1

$\overline{M}w/\overline{M}n = 1.18$

EXAMPLE 2
$\overline{M}_w/\overline{M}_n = 1.20$

EXAMPLE 3

$\overline{M}_w/\overline{M}_n = 1.21$

EXAMPLE 4
$\overline{M_w}/\overline{M_n} = 1.20$

EXAMPLE 5
$\overline{M}w/\overline{M}n = 1.16$

Example 6
$\overline{Mw}/\overline{Mn} = 1.16$

Example 11
$\bar{M}w/\bar{M}n = 1.48$

Example 12
$\bar{M}w/\bar{M}n=1.35$

Example D-2
$\bar{M}w/\bar{M}n=1.28$

Example D-3
$\bar{M}w/\bar{M}n=1.34$

BLOCK OLIGOMERS CONTAINING 2,2,6,6-TETRAMETHYL-4-PIPERIDYL GROUPS AS STABILIZERS FOR ORGANIC MATERIALS

The present invention relates to single specific block oligomers containing 2,2,6,6-tetramethyl-4-piperidyl groups, to their use as light stabilizers, heat stabilizers and oxidation stabilizers for organic materials, particularly synthetic polymers, and to the organic materials thus stabilized. Furthermore, the present invention relates to a mixture with a narrow molecular weight distribution, containing at least three different block oligomers, and to a method of the preparation thereof.

The stabilization of synthetic polymers with derivatives of 2,2,6,6-tetramethylpiperidine has been described for example in U.S. Pat. Nos. 4,086,204, 4,331,586, 4,335,242, 4,234,707, EP-A-357 223 and EP-A-377 324.

The present invention relates in particular to a compound of the formula (I)

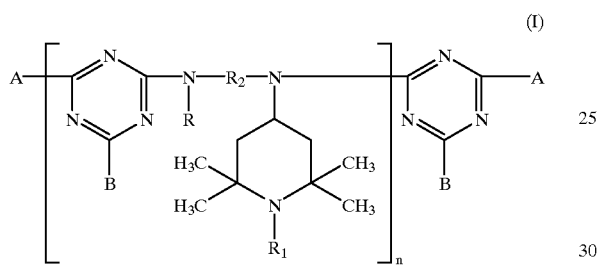

in which the polydispersity $\overline{M}w/\overline{M}n$ is 1;

n is 3, 4, 5, 6, 7, 8, 9, 10, 11, 12, 13, 14 or 15;

the radicals $R_1$ are independently of one another hydrogen, $C_1$–$C_8$alkyl, $C_2$–$C_8$hydroxyalkyl, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below except hydrogen;

or $R_2$ is a group of the formula (a), (b) or (c);

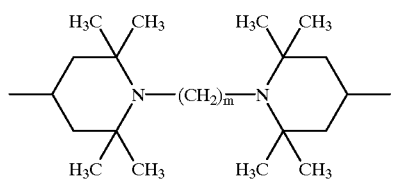

(a)

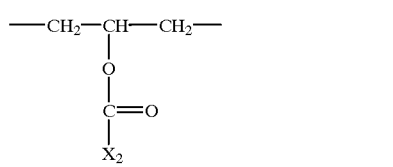

(b)

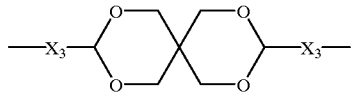

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene; the radicals A are independently of one another —$OR_3$, —$N(R_4)(R_5)$ or a group of the formula (II);

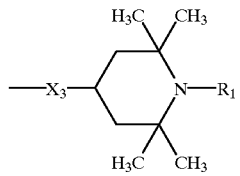

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$_4$alkyl)amino or a group of the formula (III);

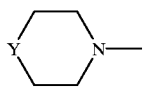

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

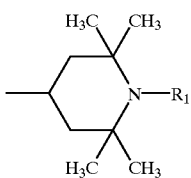
(IV)

or $C_2$–$C_4$alkyl which is substituted in the 2, 3 or 4 position by —OH, $C_1$–$C_8$alkoxy, di($C_1$–$C_4$alkyl)amino or a group of the formula (III);

R has one of the definitions given for $R_6$; and the radicals B have independently of one another one of the definitions given for A;

with the proviso that in the individual recurrent units of the formula (I), each of the radicals B, R, $R_1$ and $R_2$ has the same or a different meaning.

In the repeating units of the formula (I), the radical R and the radical

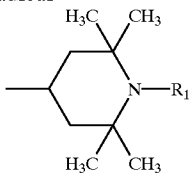

can have a random distribution or a block distribution.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

An example of $C_2$–$C_8$hydroxyalkyl and of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl) amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

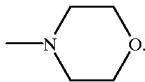

Preferred examples of $C_2$–$C_4$alkyl substituted by a group of the formula (III) are groups of the formula

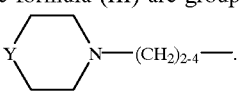

The group

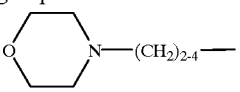

is particularly preferred.

Examples of alkoxy containing not more than 8 carbon atoms are methoxy, ethoxy, propoxy, isopropoxy, butoxy, isobutoxy, pentoxy, isopentoxy, hexoxy, heptoxy or octoxy.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

An example of $C_3$–$C_6$alkynyl is 2-butynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of ($C_1$–$C_{12}$alkoxy)carbonyl are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

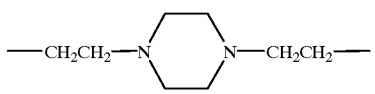

or

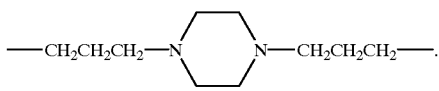

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N—$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

R is preferably hydrogen, $C_1$–$C_{10}$alkyl, cyclohexyl or a group of the formula (IV), in particular a group of the formula (IV).

The radicals $R_1$ are preferably independently of one another hydrogen, $C_1$–$C_4$alkyl, allyl, benzyl or acetyl. Hydrogen and methyl are particularly preferred.

The radical B is preferably N-(2,2,6,6-tetramethylpiperidin-4-yl)butylamino, N-(1,2,2,6,6-pentamethylpiperidin-4-yl)butylamino, dibutylamino, 1,1,3,3-tetramethylbutylamino or 4-morpholinyl.

The variable n is preferably 3, 4, 5, 6, 7, 8, 9, 10, 11, 12 or 13, for example 3, 4, 5, 6, 7, 8, 9, 10 or 11 as well as 3, 4, 5, 6, 7, 8 or 9, in particular 3, 5 or 7.

Polydispersity indicates the molecular-weight distribution of a polymeric compound. In the present application, the polydispersity is the ratio of weight-average ($\overline{Mw}$) and number-average ($\overline{Mn}$) molecular weights. A value of $\overline{Mw}/\overline{Mn}$ equal to 1 means that the compound is monodispers and has only one molecular weight and no molecular weight distribution.

A preferred embodiment of the instant invention relates to a compound of the formula (I) wherein n is 3, 4, 5, 6, 7, 8, 9, 10, 11, 12 or 13;

the radicals $R_1$ are independently of one another hydrogen, $C_1$–$C_8$alkyl, —$CH_2CN$, $C_3$–$C_6$alkenyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$-alkylenedi($C_5$–$C_7$cycloalkylene) or phenylenedi($C_1$–$C_4$alkylene);

$R_6$ is hydrogen, $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV) or $C_2$–$C_4$alkyl which is substituted in the 2, 3 or 4 position by —OH, $C_1$–$C_8$alkoxy, di($C_1$–$C_4$alkyl)amino or a group of the formula (III); and R is a group of the formula (IV).

A preferred compound of the formula (I) is that wherein $R_2$ is $C_2$–$C_{10}$alkylene, cyclohexylene, cyclohexylenedi($C_1$–$C_4$alkylene), $C_1$–$C_4$alkylenedicyclohexylene or phenylenedi($C_{1-4}$alkylene);

$R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —$N(R_4)(R_5)$ is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

A particularly preferred compound of the formula (I) is that wherein $R_2$ is $C_2$–$C_8$alkylene;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —$N(R_4)(R_5)$ is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

A compound of the formula (I) of special interest is that wherein n is 3, 5 or 7;

the radicals $R_1$ are independently of one another hydrogen or methyl;

$R_2$ is $C_2$–$C_6$alkylene; the radicals A are independently of one another —$N(R_4)(R_5)$ or a group of the formula (II);

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is >$NR_6$;

$R_6$ is $C_1$–$C_4$alkyl; and the radicals B have independently of one another one of the definitions given for A.

A further compound of the formula (I) which is of special interest is a compound of the formula (X)

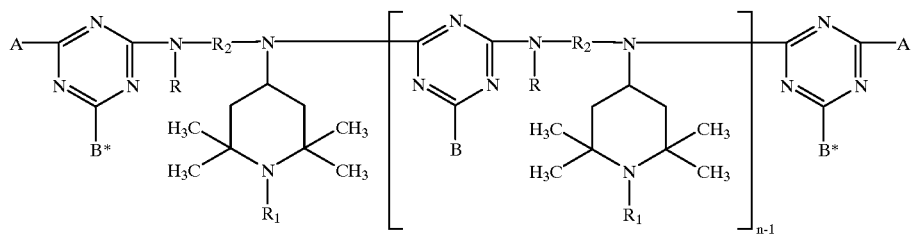

(X)

wherein n, A, B, R, $R_1$ and $R_2$ are as defined above and B* has one of the definitions given for B;

with the provisos that (1) B* is different from B and (2) each of the radicals B, R, $R_1$ and $R_2$ has the same meaning in the individual recurring units of the formula.

A preferred compound of the formula (X) is that wherein n is 3, 5 or 7;

the radicals $R_1$ are independently of one another hydrogen or methyl;

$R_2$ is $C_2$–$C_6$alkylene;

A and B*, which are identical, are —N(R$_4$)(R$_5$);

R$_4$ and R$_5$, which are identical or different, are hydrogen, C$_1$–C$_8$alkyl, 2-hydroxyethyl or 2-methoxyethyl or —N(R$_4$)(R$_5$) is additionally 4-morpholinyl;

B is a group of the formula (II) with R$_1$ being as defined above;

X is >NR$_6$;

R$_6$ is C$_1$–C$_4$alkyl; and

R is a group of the formula (IV) with R$_1$ being as defined above;

with the proviso that each of the radicals B, R, R$_1$ and R$_2$ has the same meaning in the individual recurring units of the formula.

A further embodiment of the instant invention is a mixture containing at least three different compounds of the formula (I), preferably of the formula (X), which vary only by the variable n, said mixture having a polydispersity $\overline{M}w/\overline{M}n$ of 1.1 to 1.7, for example 1.1 to 1.65, 1.1 to 1.6, 1.1 to 1.55, 1.1 to 1.5, preferably 1.1 to 1.45 or 1.1 to 1.40, in particular 1.1 to 1.35.

Further examples for the polydispersity $\overline{M}w/\overline{M}n$ are 1.15 to 1.7, for example 1.15 to 1.65, 1.15 to 1.6, 1.15 to 1.55, 1.15 to 1.5, preferably 1.15 to 1.45 or 1.15 to 1.40, in particular 1.15 to 1.35.

A preferred mixture contains a) a compound of the formula (Ia),

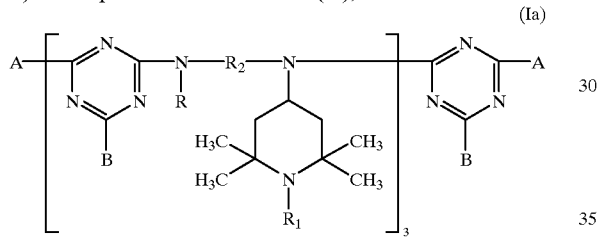

(Ia)

b) a compound of the formula (Ib) and

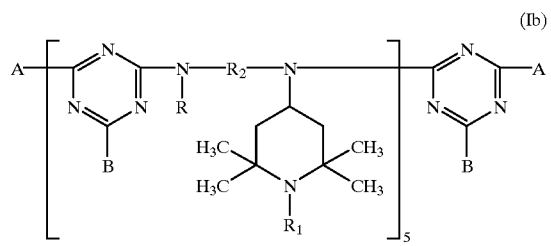

(Ib)

c) a compound of the formula (Ic)

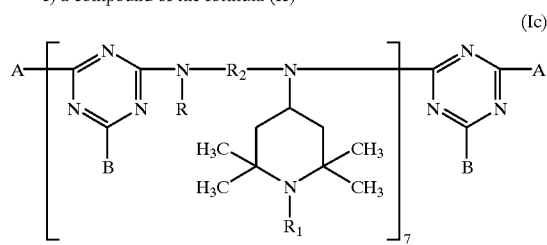

(Ic)

wherein A, B, R, R$_1$ and R$_2$ are in the formulae (Ia), (Ib) and (Ic) identical and are as defined above, and the ratio of the compounds of the formula (Ia) to (Ib) to (Ic) is 2:1.5:1 to 2:0.5:0.05, in particular 2:0.5:0.5 to 2:0.5:0.08 or 2:0.75:0.3 to 2:0.5:0.08.

The compound of the formula (Ia) corresponds preferably to a compound of the formula (Xa),

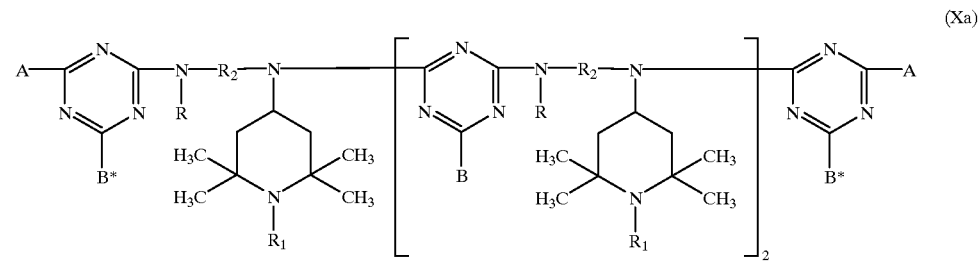

(Xa)

the compound of the formula (Ib) corresponds preferably to a compound of the formula (Xb)

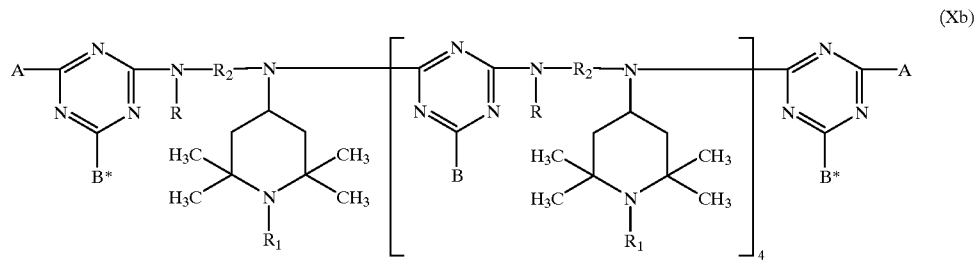

(Xb)

-continued and the compound of the formula (Ic) corresponds preferably to a compound of the formula (Xc).

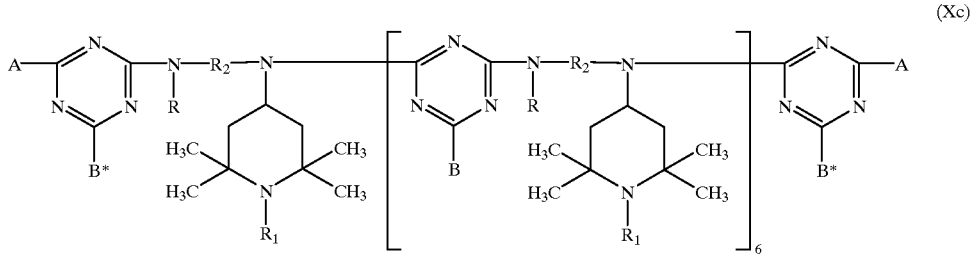

(Xc)

The indicated mixtures can additionally contain a compound of the formula (Id), for example a compound of the formula (Xd),

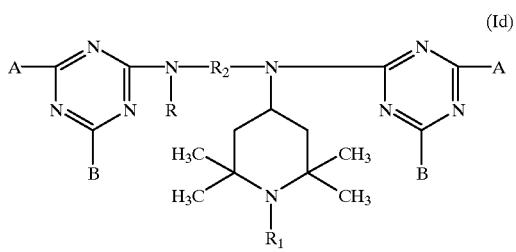

(Id)

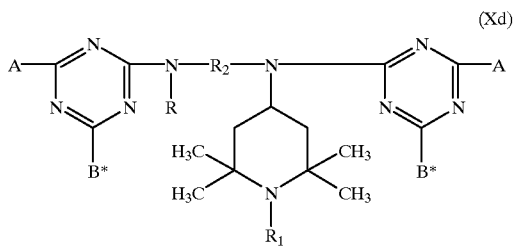

(Xd)

and/or a compound of the formula (Ie)

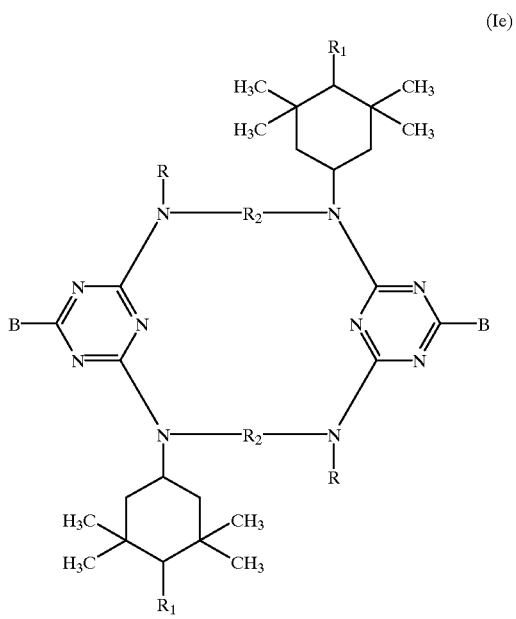

(Ie)

These compounds which are known from U.S. Pat. No. 4,108,829 and U.S. Pat. No. 4,442,250 may be present in the mixtures in an amount from 30% to 0.5%, preferably 20% to 0.5% or 8% to 0.5% with regard to the weight of the total mixture.

The preferred embodiments indicated above for the compounds of the formula (I) also relate to the mixtures thereof.

A particularly preferred mixture is one containing a compound of the formula (Ia), a compound of the formula (Ib) and a compound of the formula (Ic) wherein the radicals $R_1$ are independently of one another hydrogen or methyl;

$R_2$ is $C_2$–$C_6$alkylene;

A and B, which are identical or different, are —N($R_4$)($R_5$) or a group of the formula (II) with $R_1$ being as defined above;

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl; X is >$NR_6$;

$R_6$ is $C_1$–$C_4$alkyl; and

R is a group of the formula (IV) with $R_1$ being as defined above.

Another particularly preferred mixture is one wherein the three different compounds of the formula (I) correspond to compounds of the formulae (Xa), (Xb) and (Xc) wherein the radicals $R_1$ are independently of one another hydrogen or methyl;

$R_2$ is $C_2$–$C_6$alkylene;

A and B*, which are identical or different, are —N($R_4$) ($R_5$) or a group of the formula (II);

$R_4$ and $R_5$, which are identical or different, are hydrogen, $C_1$–$C_8$alkyl, 2-hydroxyethyl or 2-methoxyethyl or —N($R_4$)($R_5$) is additionally 4-morpholinyl;

B is a group of the formula (II) with $R_1$ being as defined above;

X is >$NR_6$;

$R_6$ is $C_1$–$C_4$alkyl; and

R is a group of the formula (IV) with $R_1$ being as defined above;

with the proviso that each of the radicals B, R, $R_1$ and $R_2$ has the same meaning in the individual recurring units of the formulae.

A and B*, which are identical or different, are preferably —N($C_1$–$C_8$alkyl)$_2$ or a group

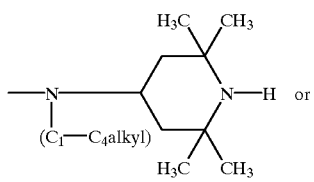 or

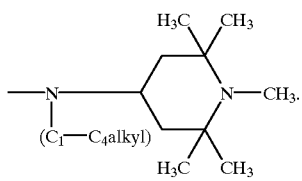

A and B* are in particular identical and are —N(C$_1$–C$_8$alkyl)$_2$.

A further embodiment of the instant invention is a method for preparing a mixture having the polydispersity indicated above and containing at least three different compounds of the formula (I), which comprises 1) reacting a compound of the formula (A)

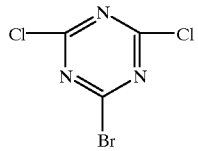

(A)

with a compound of the formula (B)

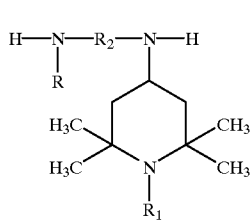

(B)

in a stoichiometric ratio to obtain a compound of the formula (C);

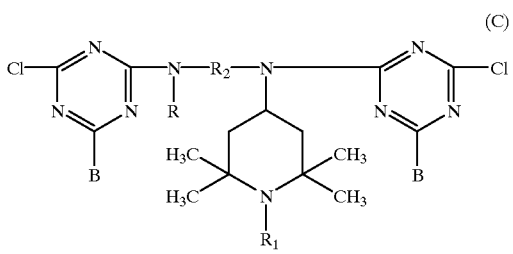

(C)

2) reacting a compound of the formula (C) with a compound of the formula (B) in a ratio of 1:2 to 1:3, preferably 1:2 to 1:2.5, in particular in a ratio of 1:2, to obtain a mixture of at least three different compounds of the formula (D) with n being 3, 4, 5, 6, 7, 8, 9, 10, 11, 12, 13, 14 or 15 or being 3, 4, 5, 6, 7, 8, 9, 10, 11, 12 or 13, preferably 3, 4, 5, 6, 7, 8, 9, 10or 11 or preferably 3, 4, 5, 6, 7, 8 or 9, in particular 3, 5 and 7;

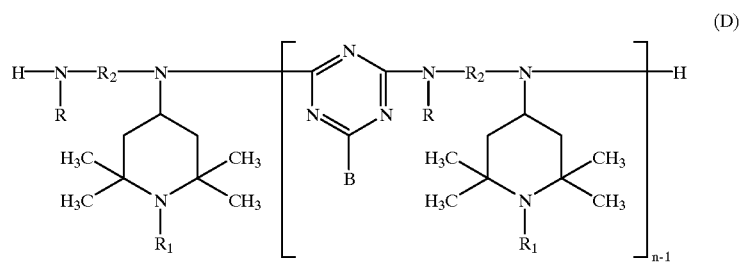

(D)

3) reacting the mixture obtained in 2) with a compound of the formula (E)

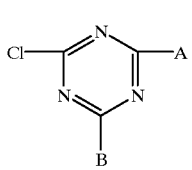

(E)

in about a stoichiometric ratio to obtain the desired mixture; the reactions 1) to 3) being carried out in an organic solvent in the presence of an inorganic base.

A particularly preferred embodiment of the instant invention relates to a method for preparing a mixture having the polydispersity indicated above and containing at least three different compounds of the formula (X), which comprises the above reactions 1) to 3) with the proviso that a compound of the formula (E*)

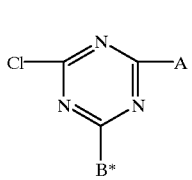

(E*)

is applied instead of a compound of the formula (E).

Examples for suitable organic solvents are toluene, xylene, trimethylbenzene, isopropylbenzene, diisopropylbenzene and essentially water-insoluble organic ketones such as for example methyl ethyl ketone and methyl isobutyl ketone. Xylene is preferred.

Examples for an inorganic base are sodium hydroxide, potassium hydroxide, sodium carbonate and potassium carbonate. Sodium hydroxide is preferred.

The reaction 1) is carried out, for example, at a temperature of 40° C. to 70° C., preferably 50° C. to 60° C.

The reaction 2) is carried out, for example, at a temperature of 110° C. to 180° C., preferably 140° C. to 160° C.

The reaction 3) is carried out, for example, at a temperature of 110° C. to 180° C., preferably 140° C. to 160° C.

Possible by-products are the above shown compounds of the formulae (Id) and (Ie).

The compound of the formula (A) can be prepared, for example, by reacting cyanuric chloride with a compound B–H in a stoichiometric ratio in the presence of an organic solvent and an inorganic base.

Furthermore, the compound of the formula (E) or (E*) can be prepared, for example, by reacting cyanuric chloride with compounds of the formulae A–H and B–H or B*–H in a stoichiometdc ratio in the presence of an organic solvent and an inorganic base.

It is appropriate to use for the preparation of the compounds of the formulae (A) and (E) or (E*) the same solvent and the same inorganic base than in the above indicated reactions 1) to 3).

The starting materials used in the above process are known. In the case that they are not commercially available, they can be prepared analogously to known methods. For example, some starting materials of the formula (B) are described in WO-A-95/21157, U.S. Pat. No. 4,316,837 and U.S. Pat. No. 4,743,688.

An embodiment of the instant invention is also a mixture obtainable by the above indicated method.

The intermediates of the formula (D) are novel and are a further embodiment of the instant invention. In addition, the instant invention relates to a mixture containing at least three different compounds of the formula (D) which vary only by the variable n, said mixture having a polydispersity $\overline{M}w/\overline{M}n$ of 1.1 to 1.7.

The preferred embodiments of the variable n and the radicals R, $R_1$, $R_2$ and B indicated above for the compounds of the formula (I) also relate to the intermediates of the formula (D).

A compound of the formula (I) or (D) with a polydispersity $\overline{M}w/\overline{M}n$ of 1 may be prepared by building up said compound step by step. Some representative examples for such a procedure are shown below.

I) A compound of the formula (I) wherein R is a group of the formula (IV) and n is 3 may conveniently be prepared by reacting a compound of the formula (E) with a large excess of a compound of the formula (B) to obtain a compound of the fomula (F) according to Scheme I-1. The molar ratio of the compound of the formula (E) to the compound of the formula (B) may be for example 1:4.

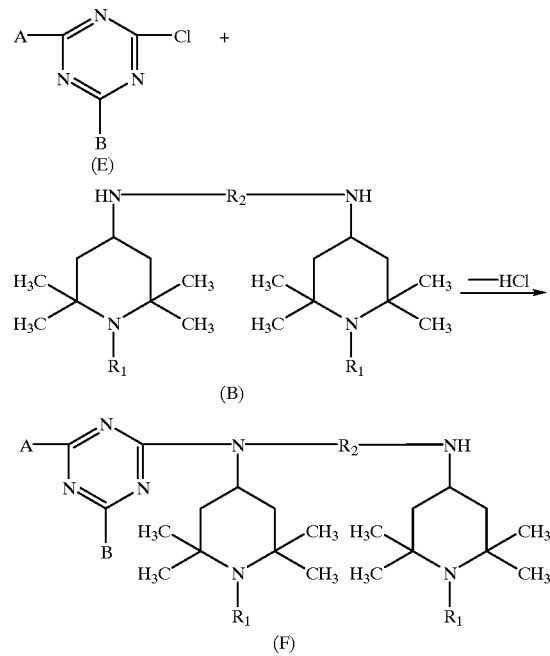

Subsequently, the compound of the formula (F) may be reacted with the compound of the formula (C) in a stoichiometric ratio to obtain the desired compound as shown in Scheme I-2.

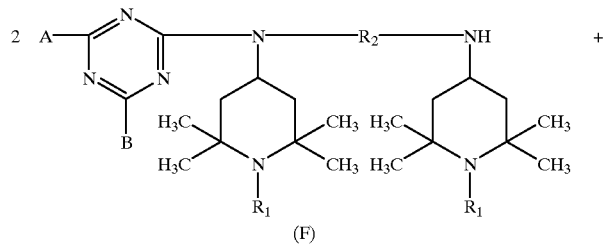

-continued

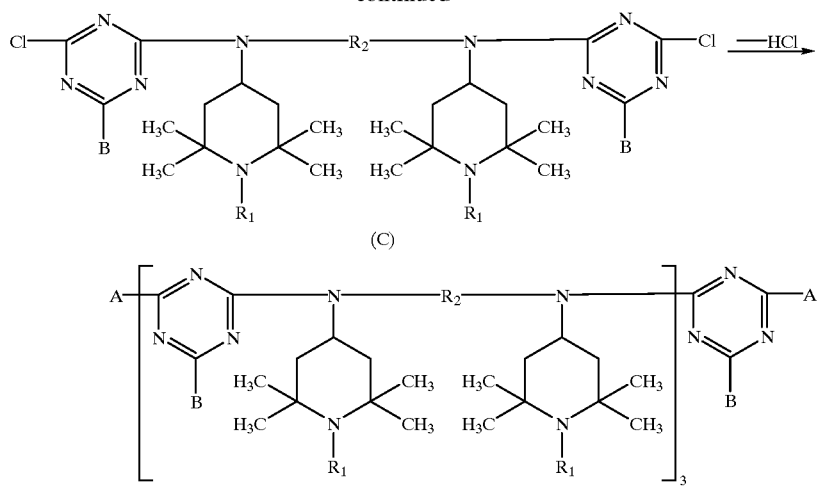

II) A compound of the formula (I) wherein R is a group of the formula (IV) and n is 4 may conveniently be prepared by reacting a compound of the formula (F) with a compound of the formula (A) in a stoichiometric ratio to obtain a compound of the formula (G) according to Scheme II-1.

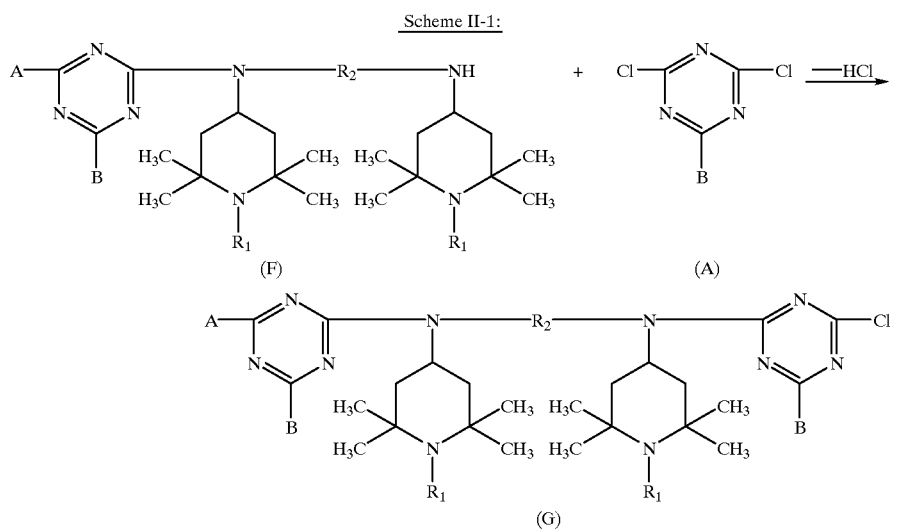

Then, the compound of the formula (G) may be reacted with a large excess of a compound of the formula (B) to obtain a compound of the formula (H) as shown in Scheme II-2. The molar ratio of the compound of the formula (G) to the compound of the formula (B) may be for example 1:4.

Scheme II-2:

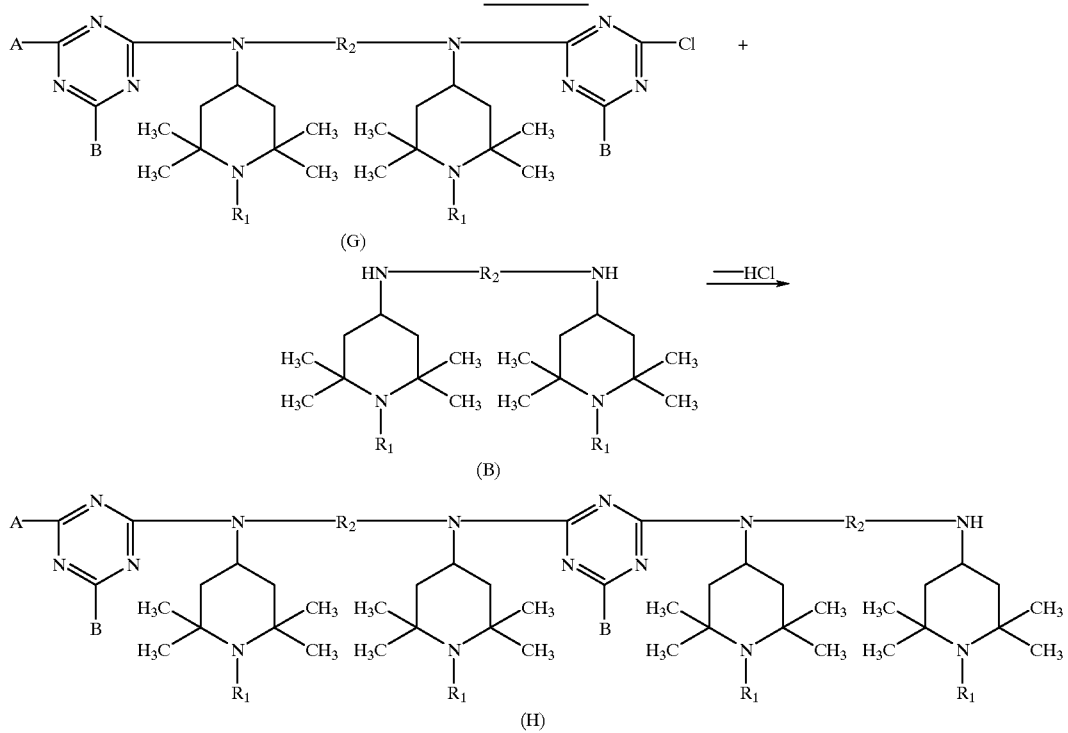

Subsequently, the compound of the formula (H) may be reacted with a compound of the formula (A) in a stoichiometric ratio to obtain a compound of the formula (K), following the Scheme II-3.

Scheme II-3:

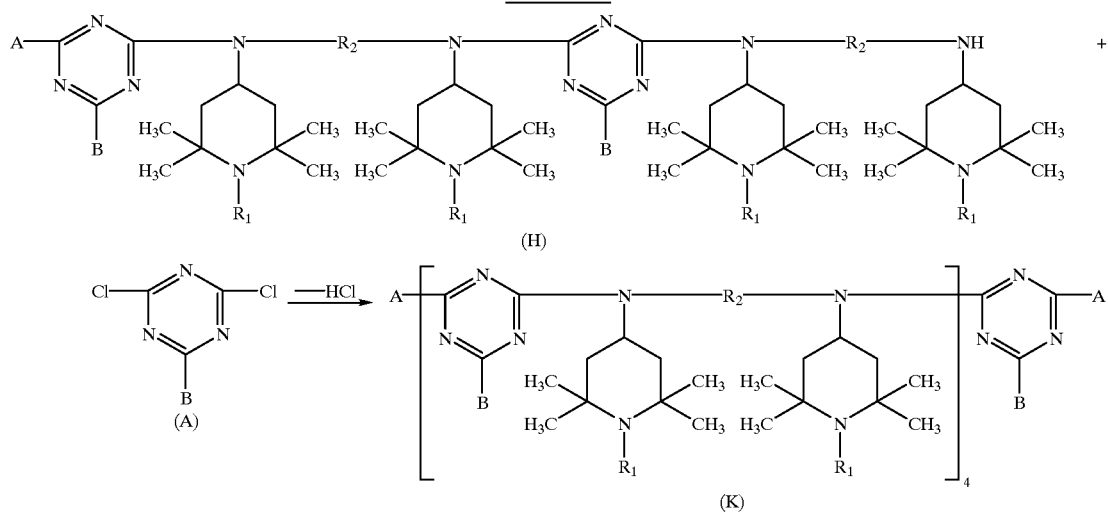

III) A compound of the formula (I) wherein R is a group of the formula (IV) and n is 5 may conveniently be prepared by reacting a compound of the formula (H) with a compound of the formula (C) in a stoichiometric ratio to obtain a compound of the formula (L)

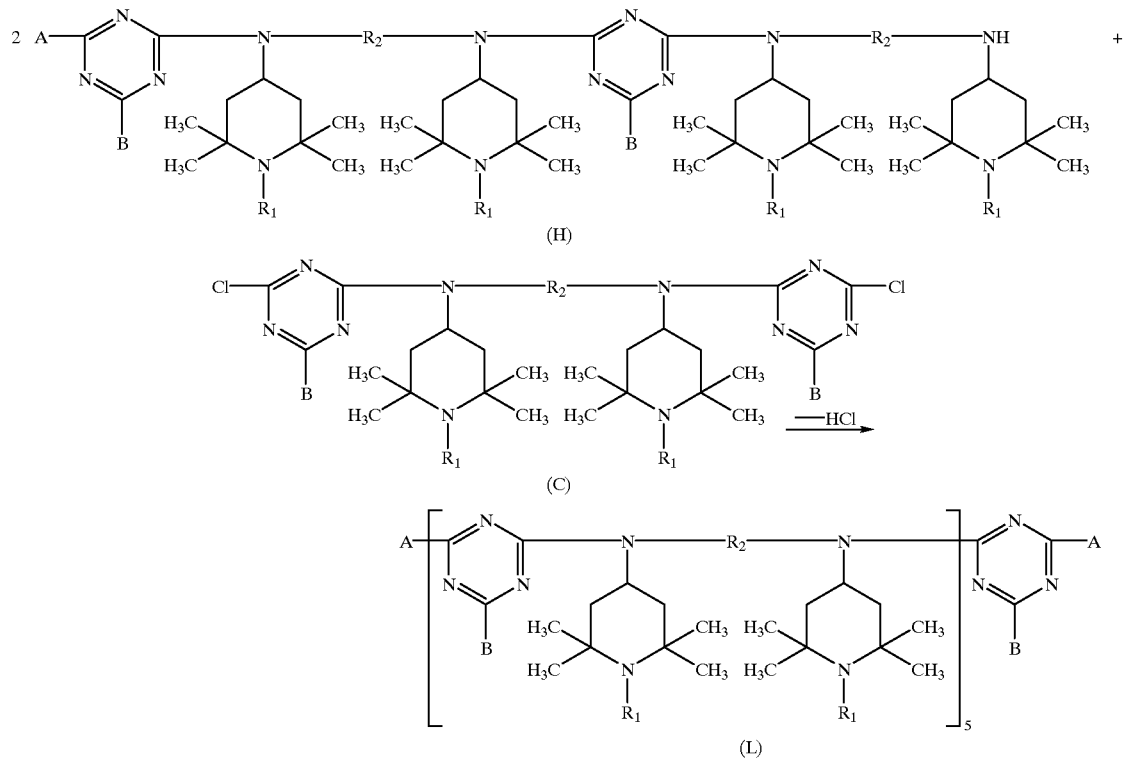

The reactions I) to III) are carried out, for example, in an organic solvent such as toluene, xylene, trimethylbenzene in the presence of an inorganic base such as sodium hydroxide at a temperature of 110° C. to 180° C., preferably 140° C. to 160° C.

When the compound of the formula (I) corresponds to a compound of the formula (X), the corresponding compounds of the formulae (Xa), (Xb) and (Xc) may be prepared in analogy to the above schemes by using a compound of the formula (E*) instead of a compound of the formula (E).

The intermediate of the formula (D) wherein n is for instance 3 and which has a polydispersity $\overline{M}w/\overline{M}n$ of 1 may be prepared, for example, by reacting a compound of the formula (C) with a compound of the formula (B) in a ratio of 1:10 to 1:50, preferably 1:20 to 1:40, in particular 1:20 to 1:35. The reaction may be carried out e.g. in an organic solvent or neat in the presence of an inorganic base. The solvent and/or the excess of the reactant of the formula (B) can be eliminated by distillation at the appropriate conditions. Examples for an organic solvent are toluene, xylene, trimethylbenzene, isopropylbenzene and diisopropylbenzene. Xylene is preferred. Examples for an inorganic base are sodium hydroxide, potassium hydroxide, sodium carbonate and potassium carbonate. Sodium hydroxide is preferred. The reaction is carried out at a temperature of, for example, 110° C. to 180° C., preferably 140° C. to 160° C.

The compounds of the formula (I) as well as the described mixtures with a narrow molecular weight distribution are very effective in improving the light, heat and oxidation resistance of organic materials, especially synthetic polymers and copolymers. In particular, a low pigment interaction as well as a very good colour is observed in polypropylene, especially polypropylene fibres.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or poly tetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenolF, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and at least one compound of the formula (I), preferably formula (X), with a polydispersity $\overline{M}w/\overline{M}n=1$, with the proviso that the totality of the compounds of the formula (I) being present in the composition has a polydispersity $\overline{M}w/\overline{M}n$ of 1 to 1.7, for example 1 to 1.65, 1 to 1.6, 1 to 1.55, 1 to 1.5, 1 to 1.45, 1 to 1.4 or 1 to 1.35.

The invention further relates to a composition comprising an organic material susceptible to degradation induced by light, heat or oxidation and a mixture containing at least three different compounds of the formula (I), preferably formula (X), which vary only by the variable n, said mixture having a polydispersity $\overline{M}w/\overline{M}n$ of 1.1 to 1.7 or 1.1 to 1.5, with the proviso that the totality of the compounds of the formula (I) being present in the composition has a polydispersity $\overline{M}w/\overline{M}n$ of 1.1 to 1.7 or 1.1 to 1.5.

The organic material is preferably a synthetic polymer, more particularly one selected from the aforementioned groups. Polyolefins are preferred and polyethylene and polypropylene are particularly preferred.

A further embodiment of the instant invention is a method for stabilizing an organic material against degradation induced by light, heat or oxidation, which comprises incorporating into said organic material at least one compound of the formula (I), preferably formula (X), with a polydispersity $\overline{M}w/\overline{M}n=1$, with the proviso that the totality of the compounds of the formula (I) being present in the composition has a polydispersity $\overline{M}w/\overline{M}n$ of 1 to 1.7, preferably 1 to 1.5 or 1 to 1.4, in particular 1 to 1.35.

The compounds of the formula (I) or a mixture thereof can be used in various proportions depending on the nature of the material to be stabilized, on the end use and on the presence of other additives.

In general, it is appropriate to use, for example, 0.01 to 5% by weight of the compounds of the formula (I) or the mixture thereof, relative to the weight of the material to be stabilized, preferably 0.05 to 1%.

The compounds of the formula (I) or the mixture thereof can be added, for example, to the polymeric materials before, during or after the polymerization or crosslinking of the said materials. Furthermore, they can be incorporated in the polymeric materials in the pure form or encapsulated in waxes, oils or polymers.

In general, the compounds of the formula (I) or the mixture thereof can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the compounds of the formula (I) or the mixture thereof can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of the formula (I) or mixtures thereof.

Particular examples of said conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-di-methylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α(o-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis (5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis( 4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)-isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydronxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)-hydrazine.

1.18. Ascorbic acid (vitamin C)

1.19. Aminic antioxidants, for example N,N'-di-isopropyl-p-phenylenediamine, N,N'-di-secbutyl-p-phenylenediamine, N,N'-bis(1,4-dimethylpentyl)-p-phenylenediamine, N,N'-bis( 1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naph-thyl)-p-phenylenediamine, N-isopropyl-N'-phenyl-p-phenylenediamine, N-(1,3-dimethylbutyl)-N'-phenyi-p-phenylenediamine, N-(1-methylheptyl)-N'-phenyl-p-phenylenediamine, N-cyclo-hexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopro-pyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-buty/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1.2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol300;, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-di-phenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-di-chloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-do-decylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tertbutoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-di-methylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal- N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8, 10-tetra-tert-butyl-12H-di-benz[d,g]-1,3,2-dioxaphosphocin, 6-fluoro-2,4,8,10-tetra-tert-butyl- 12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylamines, for example, N,N-dibenzylhydroxylamine, N,N-diethylhydroxylamine, N,N-dioctylhydroxylamine, N, N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863, 4,338,244, 5,175,312, 5,216,052, 5,252,643, DE-A-4316611, DE-A-4316622, DE-A-4316876, EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The compounds of the formula (I) or the mixtures thereof can also be used as stabilizers, especially as light stabilizers, for almost all materials known in the art of photographic reproduction and other reproduction techniques as e.g. described in Research Disclosure 1990, 31429 (pages 474 to 480).

The weight ratio of the compounds of the formula (I) or the mixture thereof to the conventional additives may be 1:0.5 to 1:5.

The compounds of the formula (I) or mixtures thereof are particularly useful for stabilizing pigmented polyolefins, in particular polypropylene.

The explanations and comments given above for the compounds of the formula (I) and mixtures thereof with regard to the stabilization of organic materials are also applicable to the intermediates of the formula (D) and mixtures thereof.

The invention is illustrated in more detail by the following Examples. All percentages are by weight, unless otherwise indicated.

GPC (Gel Permeation Chromatography) is used as an analytical procedure for separating molecules by their difference in size and to obtain molecular weight averages($\overline{M}w$, $\overline{M}n$) or information on the molecular weight distribution of polymers.

The technique is well known and described, for instance, in "Modem Size—Exclusion Liquid Chromatography" by W. W. Yan et al., edited by J. Wiley & Sons, N.Y., USA, 1979, pages 4–8, 249–283 and 315–340.

A narrow molecular weight distribution is characterized by a polydispersity ($\overline{M}w/\overline{M}n$) close to 1.

The GPC analyses shown in the following Examples are carried out with a GPC chromatograph ®Perkin-Elmer LC 250 equipped with ®Perkin-Elmer RI detector LC 30 and with ®Perkin-Elmer oven LC 101.

All the analyses are carried out at 45° C. by using three columns PLGEL 3 μm Mixed E 300 mm lenght×7.5 mm i.d.(from Polymers Laboratories Ltd. Shropshire, U.K).

Tetrahydrofurane is used as eluant (flow 0.40 ml/min) and the samples are dissolved in tetrahydrofurane (2%) (% w/v).

In the structural formulae of the following examples, n' indicates that there are repetitive units in the molecules and the products obtained are not uniform. These products are characterized by the number average molecular weight $\overline{M}n$ and the polydispersity $\overline{M}w/\overline{M}n$.

BRIEF DESCRIPTION OF THE DRAWINGS

The drawings of FIGS. 1–15 represent chromatograms of the products prepared in working Examples 1–6, 6/bis, 10–12 and D-1 to D-5 respectively. They demonstrate the narrow molecular weight distribution of the instant products as characterized by a polydispersity ($\overline{M}w/\overline{M}n$) of close to 1.

The products described in Examples 1, 2, 5, 6 and 10, in particular Example 10, relate to a preferred embodiment of the instant invention.

EXAMPLE 1

Figure 1:
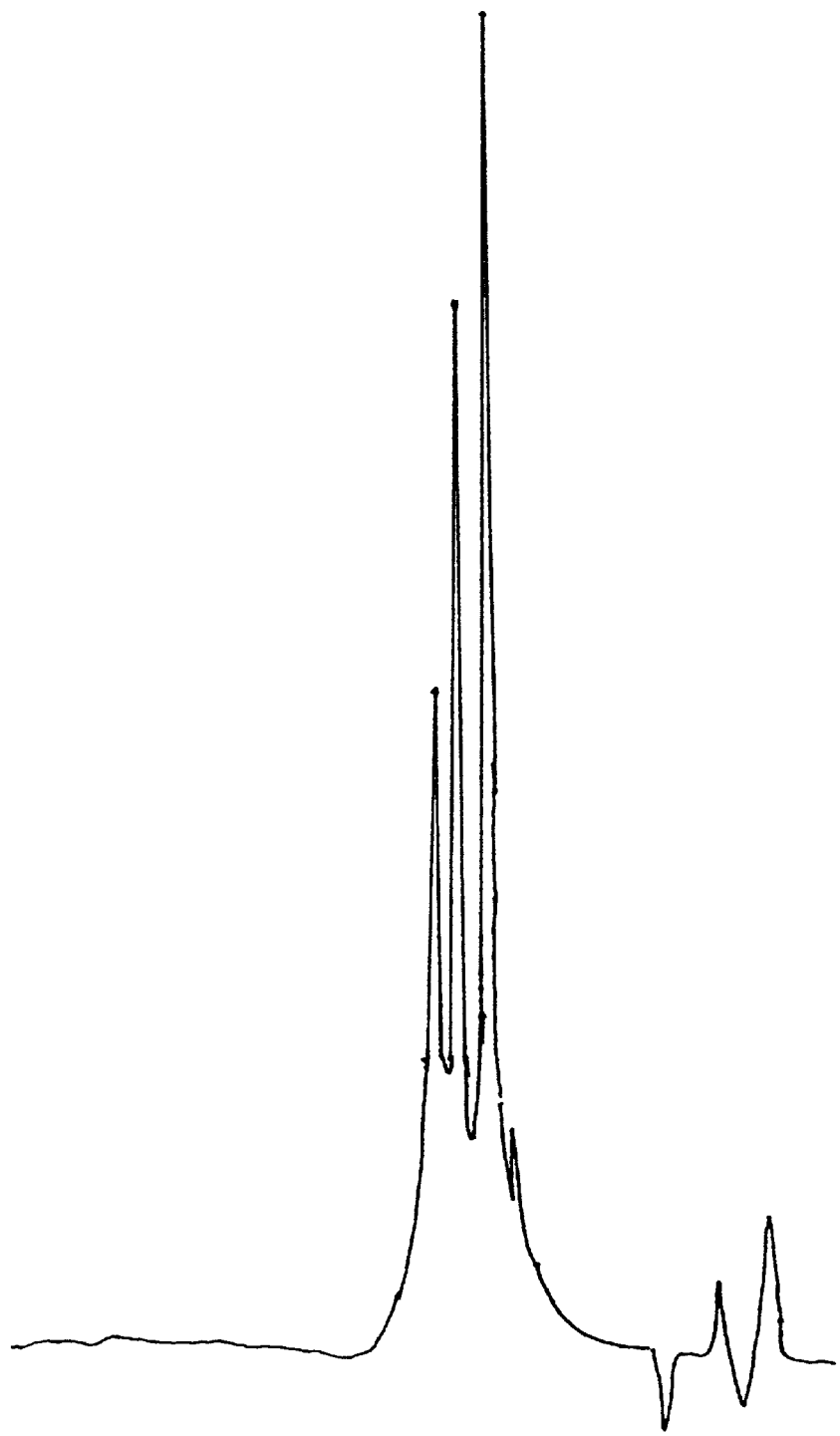

Preparation of the compound of the formula

A solution of 74.3 g (0.35 moles) of N-(2,2,6,6-tetramethyl-4-piperidinyl)-n-butylamine in 50 ml of water is added slowly, at 0° C. to a solution of 64.5 g (0.35 moles) of cyanuric chloride in 500 ml of xylene, keeping the temperature during the addition and for further 1 hour.

After 2 hours at room temperature the mixture is cooled to 0° C. and an aqueous solution of 14.7 g (0.368 moles) of sodium hydroxide in 50 ml of water is added. After ½ hour at 0° C. and further 2 hours at room temperature, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour and 48.4 g (0.35 moles) of ground potassium carbonate are added and heated to 60° C. for 4 hours.

After washing with water, the organic phase is concentrated under vacuum at 60–70° C./10 mbar, being 250 ml of xylene recovered. 138.1 g (0.35 moles) of N,N'-bis(2,2,6,6-tetramethyl-4-piperidinyl)-1,6-hexanediamine are added and the mixture is heated to 150° C. for 2 hours, cooled again and added with 14 g (0.35 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 300 ml of xylene, filtered and washed three times with 100 ml of ethylene glycol.

After concentrating under vacuum at 60° C./10 mbar 78.7 g (0.147 moles) of 2-chloro-4,6-bis[N-(2,2,6,6-tetramethyl-4-piperidinyl)-n-butylamino]-1,3,5-triazine are added.

The mixture is heated to 140° C. for 3 hours and 5.9 g (0.147 moles) of ground sodium hydroxide are added, being the mixture heated to reflux and being the reaction water eliminated off azeotropically.

The mixture is heated to 160° C. for 4 hours, added with further 5.9 g (0.147 moles) of ground sodium hydroxide and heated again to 160° C. for 2 hours.

After cooling to 60° C., the mixture is diluted with 300 ml of xylene, filtered and concentrated under vacuum at 140° C./1 mbar.

A solid is obtained with m.p. (melting point)=166–170° C. after drying.

$\overline{M}n$ (by GPC)=3360 g/mol $\overline{M}w/\overline{M}n$=1.18

The GPC analysis shows a chromatogram as in FIG. 1.

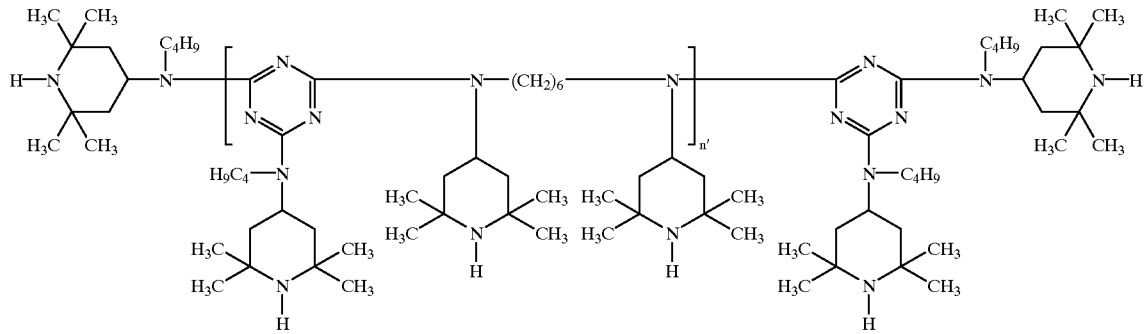

EXAMPLE 2

Preparation of the compound of the formula

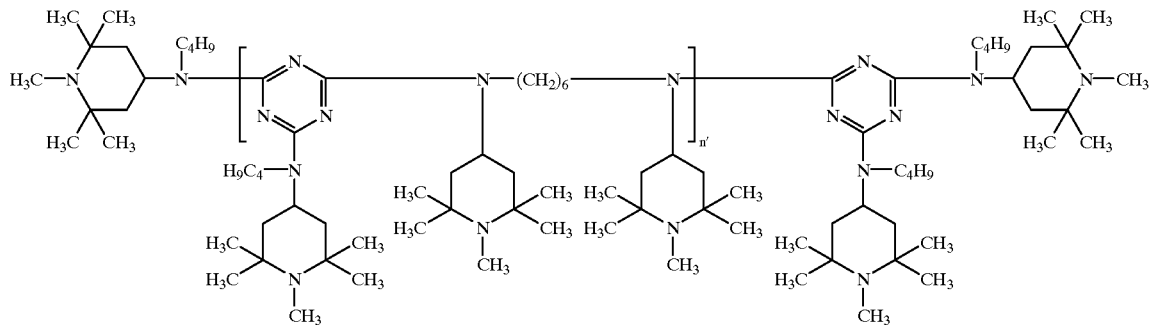

A mixture of 6.6 g (0.143 moles) of formic acid and of a solution obtained by dissolving 4.3 g (0.143 moles) of paraformaldehyde in 16 ml of 2% (w/v) aqueous NaOH solution is added slowly to a solution of 11 g of the compound of the Example 1 in 50 ml of xylene and heated to 110° C., the water added and the water of reaction simultaneously being separated off azeotropically.

The mixture is then cooled to 70–80° C. and a solution of 4 g of sodium hydroxide in 20 ml of water is added at 30–80° C.

The aqueous layer is separated off and the mixture is dehydrated, separating off the water azeotropically.

After evaporation in vacuum (140° C./1 mbar) a product with m.p. 184–190° C. is obtained.

$\overline{M}n$ (by GPC)=3650 g/mol $\overline{M}w/\overline{M}n$=1.20

Figure 2:
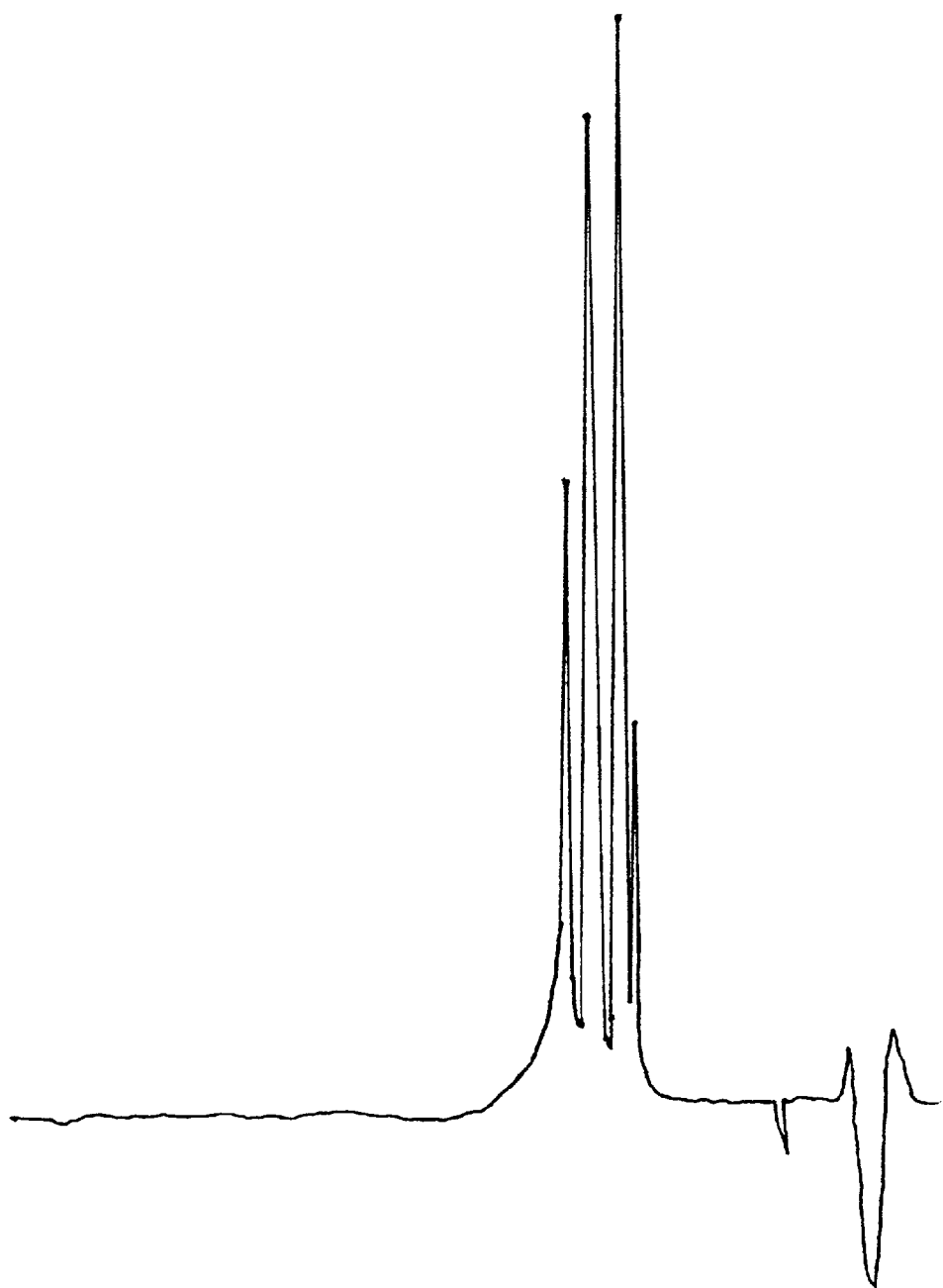

The GPC analysis shows a chromatogram as in FIG. 2.

EXAMPLE 3–6

Following the procedure described in Example 1, under the same reaction conditions and using the appropriate reagents, the following compounds of the formula (I) are prepared.

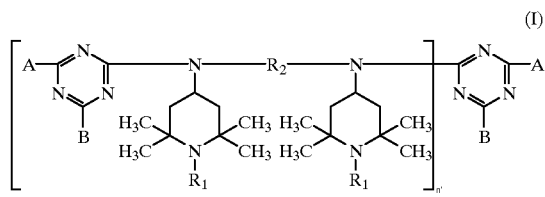

Figure 3:
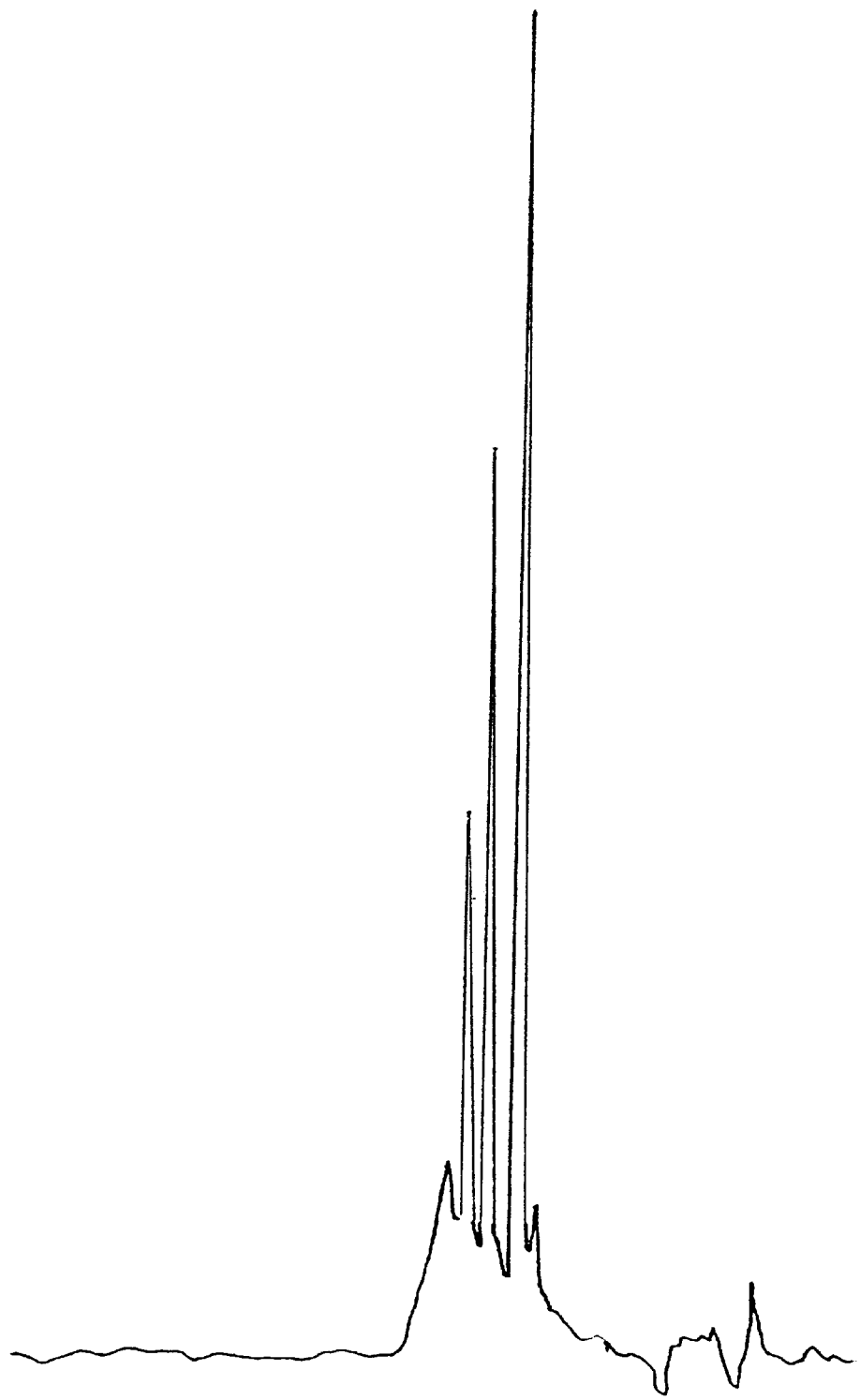
Figure 4:
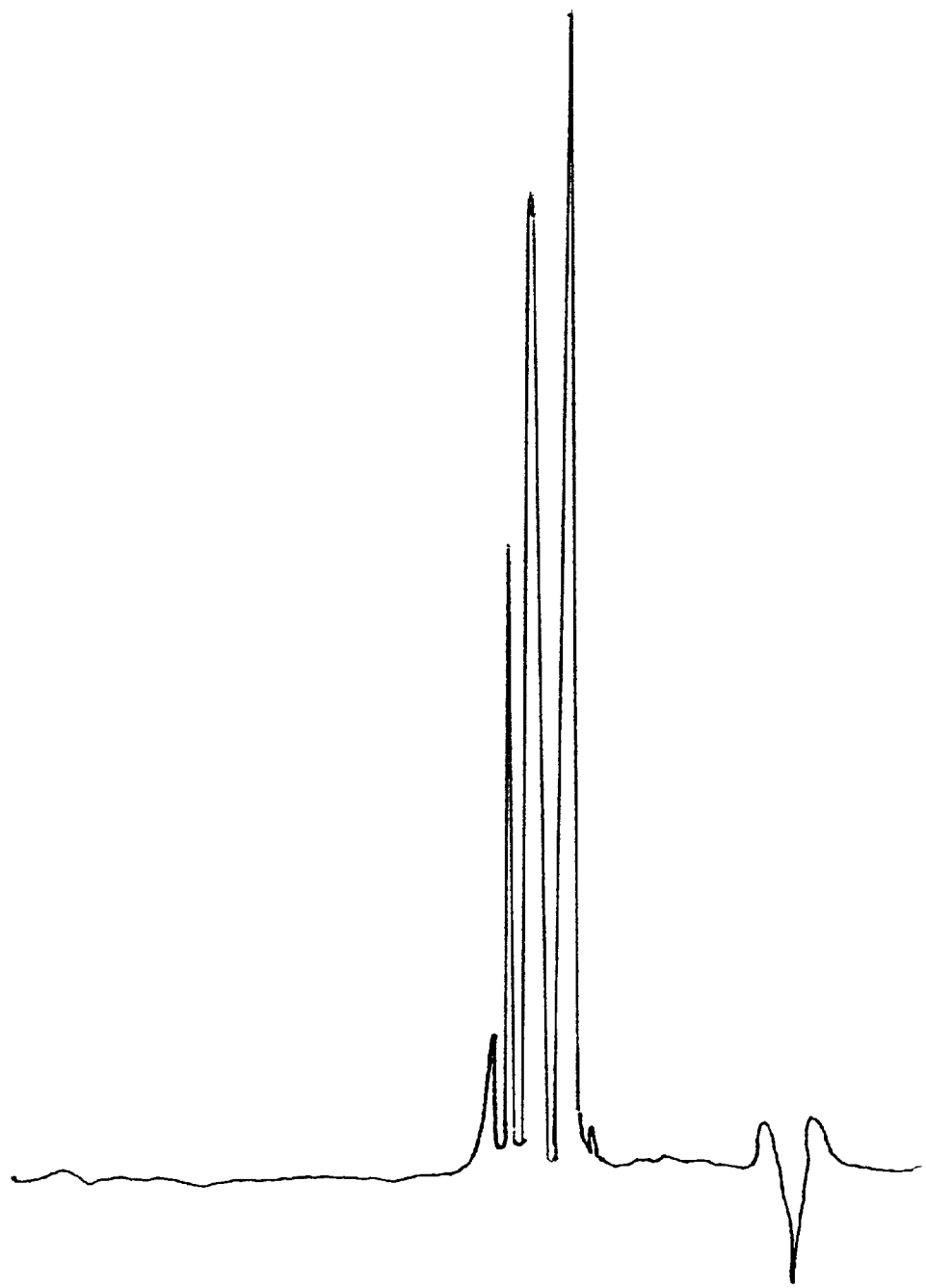
Figure 5:
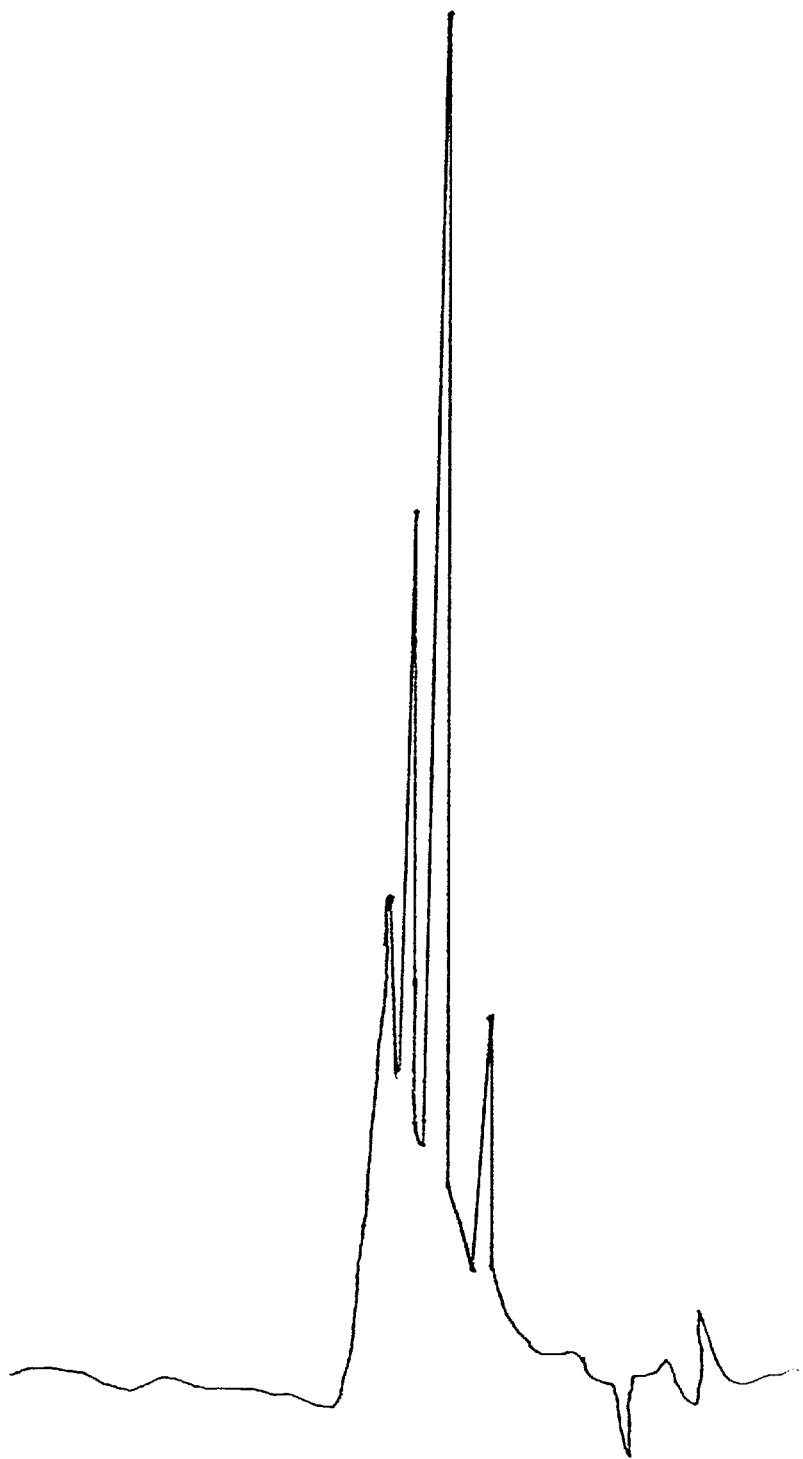
Figure 6:
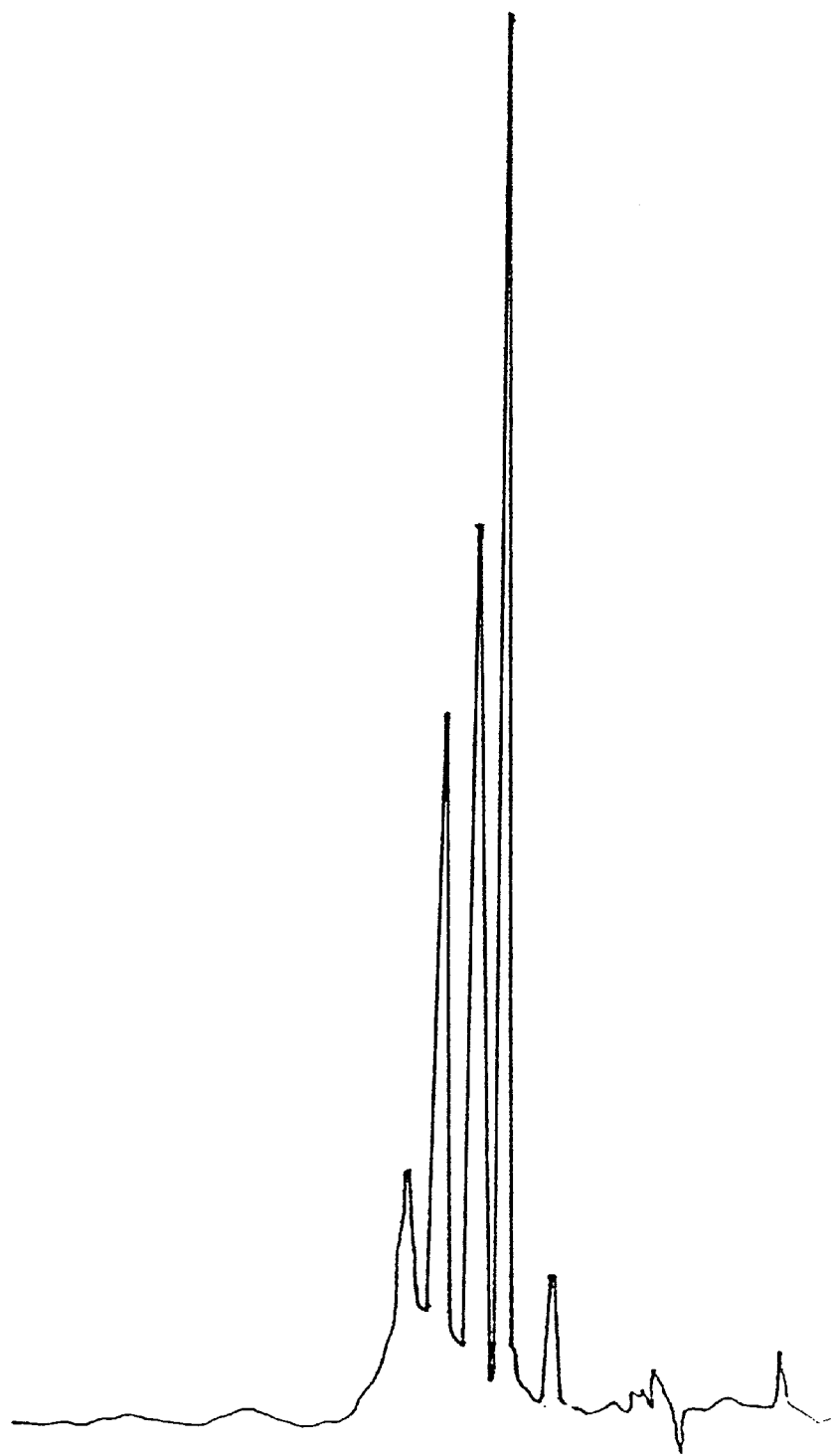

| Example | A | B | $R_1$ | $R_2$ | $\overline{M}n$ | $\overline{M}w/\overline{M}n$ (GPC analysis) | m.p.(° C.) |
|---|---|---|---|---|---|---|---|
| 3 | morpholino-N | morpholino-N | —H | —(CH$_2$)$_6$— | 2450 | 1.21 (FIG. 3) | 152–159 |
| 4 | morpholino-N | morpholino-N | —CH$_3$ | —(CH$_2$)$_6$— | 2770 | 1.20 (FIG. 4) | 180–187 |
| 5 | (C$_4$H$_9$)$_2$N— | (C$_4$H$_9$)$_2$N— | —H | —(CH$_2$)$_6$— | 3870 | 1.16 (FIG. 5) | 85–95 |
| 6 | (C$_4$H$_9$)$_2$N— | (C$_4$H$_9$)$_2$N— | —CH$_3$ | —(CH$_2$)$_6$— | 4060 | 1.16 (FIG. 6) | 98–106 |

-continued

Figure 7:
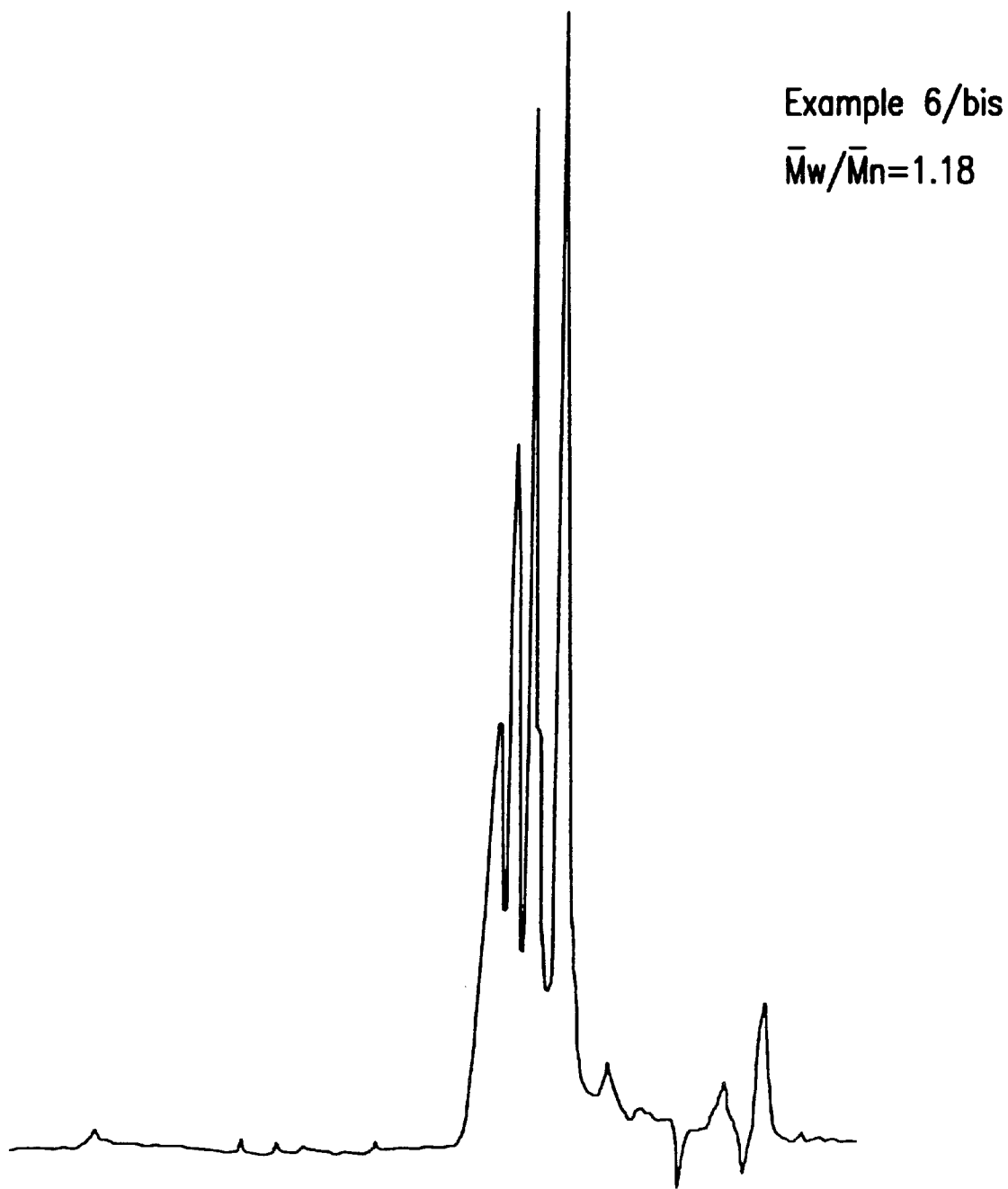

| Example | A | B | R$_1$ | R$_2$ | $\overline{M}n$ | $\overline{M}w/\overline{M}n$ (GPC analysis) | m.p.(° C.) |
|---|---|---|---|---|---|---|---|
| 6/bis | ![A structure] | ![B structure] | —H | —(CH$_2$)$_6$— | 3340 | 1.18 (FIG. 7) | 115–125 |

EXAMPLE 7

Preparation of the compound of the formula

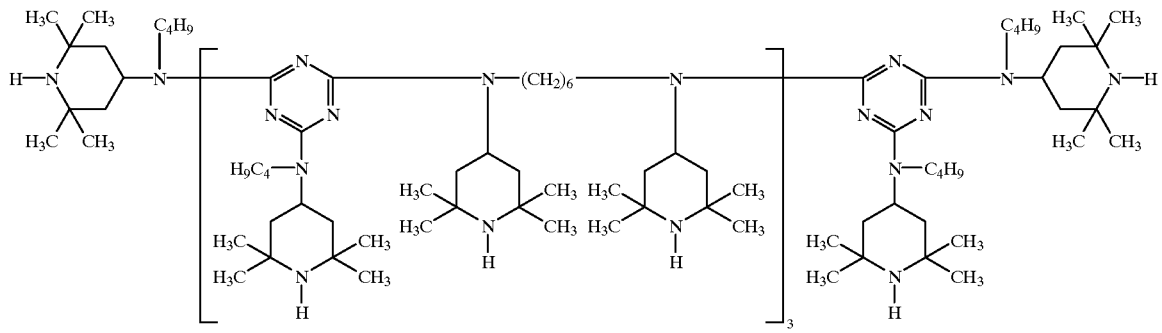

a) Preparation of N,N'-dibutyl-N,N',N''-tris-(2,2,6,6-tetramethyl-4-piperidinyl)-N''-[6-(2,2,6,6-tetramethyl-4-piperidinylamino)-hexyl]-[1,3,5]-triazine-2,4,6-triamine.

A solution of 53.5 g (0.1 mole) of 2-chloro-4,6-bis[N-(2,2,6,6-tetramethyl-4-piperidinyl)-n-butylamino]-1,3,5-triazine in 250 ml of xylene is added slowly at reflux temperature to a solution of 157.9 g (0.4 moles) of N,N'-bis(2,2,6,6-tetramethyl-4-piperidinyl)-1,6-hexane diamine in 250 ml of xylene.

After the addition, 8 g (0.2 moles) of sodium hydroxide are added and the mixture is heated to reflux for 8 hours.

The mixture is then filtered and the solution is concentrated under vacuum (140° C./1 mbar) and the excess of N,N'-bis(2,2,6,6-tetramethyl-4-piperddinyl)-1,6-hexane is eliminated off under vacuum (190° C./0.2 mbar).

The solid so obtained is dissolved in 200 ml of xylene and washed four times with water (50 ml) and dried on Na$_2$SO$_4$.

After filtration the xylene solution is evaporated under vacuum (140° C./10 mbar) and, after drying, a product with m.p. 67–72° C. is obtained.

Analysis for C$_{53}$H$_{103}$N$_{11}$: Calculated: C=71.17%; H=11.61%; N=17.22%; Found: C=70.47%; H=11.49%; N=17.09%;

b) Preparation of N,N'-bis[4-[(2,2,6,6-tetramethyl-4-piperidinyl)-butylamino]-6-chloro-[1,3,5]-triazin-2-yl]-N,N'-bis(2,2,6,6-tetramethyl-4-piperidinyl)-1,6-hexanediamine.

To a solution of 36.03 g (0.1 mole) of 2,4-dichloro-6-[(2,2,6,6-tetramethyl-4-piperidinyl)-butylamino]-[1,3,5]-triazine in 200 ml of xylene, 19.7 g (0.05 moles) of N,N'-bis(2,2, 6, 6-tetramethyl-4-piperidinyl)-1,6-hexanediamine are added.

The mixture is heated to 50° C. for 1 hour and 15.2 g (0.11 moles) of ground potassium carbonate are added and heated to 60° C. for 4 hours.

The mixture is cooled, filtered and washed twice with 50 ml of water.

The organic phase is dried on sodium sulfate, filtered and evaporated under vacuum (100° C./10 mbar).

After drying a solid is obtained with m.p. 100–103° C.

Analysis for organic chlorine: Calculated: 6.80%; Found: 6.78%;

c) Preparation of the compound of the above shown formula.

A solution of 35.7 g (0.04 moles) of the compound prepared as in a) and 20.8 g (0.02 moles) of the compound prepared as in b) in 200 ml of xylene is heated to reflux for 3 hours.

The mixture is added to 3.2 g (0.08 moles) of ground sodium hydroxide and heated to reflux being the reaction water eliminated off azeotropically. The mixture is heated to 190° C. in a closed vessel for 14 hours, cooled and filtered.

The organic solution is washed three times with water (50 ml) dried on sodium sulfate, filtered and evaporated under vacuum (140° C./1 mbar).

After drying a product is obtained with m.p. 150–155° C.

Analysis for C$_{162}$H$_{306}$H$_{36}$: Calculated: C=70.54%; H=11, 18%; N=18.28%; Found: C=70.34%; H=11.10%; N=18.06%;

EXAMPLE 8

Preparation of the compound of the formula

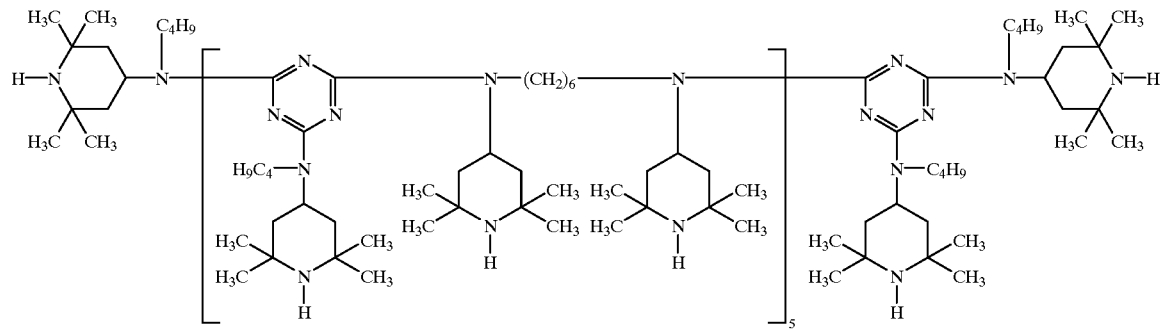

a) Preparation of the compound of the formula

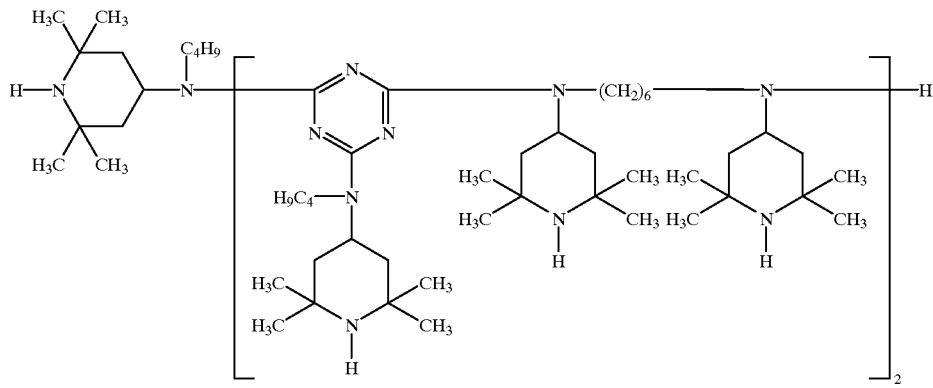

A solution of 20 g (0.022 moles) of the compound prepared as described in example 7 a) and 8.1 g (0.022 moles) of 2,4-dichloro-6-[(2,2,6,6-tetramethyl-4-piperidinyl)-butylamino]-1,3,5-triazine in 100 ml of xylene is heated to 40° C. for 1 hour.

3.1 g (0.022 moles) of ground potassium carbonate is added and the mixture is heated to 60° C. for 2 hours, to 80° C. for 1 hour and cooled to room temperature.

34.7 g (0.088 moles) of N,N'-bis(2,2,6,6-tetramethyl-4-piperidinyl)-1,6-hexanediamine and 0.88 g (0.022 moles) of ground sodium hydroxide are added.

The mixture is heated to reflux for 15 hours, being the reaction water eliminated off azeotropically.

After cooling, the mixture is filtered and the organic solution washed three times with ethylene glycol (50 ml) and three times with water (50 ml).

The organic solution is then dried under sodium sulfate, filtered and evaporated under vacuum (140° C./0.1 mbar).

A solid product is obtained with m.p. 110–115° C.

Analysis for $C_{93}H_{178}N_{20}$: Calculated: C=70.85%; H=11.38%; N=17.77%; Found: C=70.34%; H=11.26%; N=17.52%;

b) Preparation of the compound of the above shown formula.

A solution of 10 g (0.0063 moles) of the compound prepared as in a) and 3.3 g (0.00315 moles) of the compound prepared as in Example 7 b) in 100 ml of trimethylbenzene is heated to reflux for 3 hours and added with 1.75 g (0.013 moles) of ground potassium carbonate.

The mixture is heated to reflux for 24 hours, being the reaction water eliminated off azeotropically.

The mixture is cooled, filtered and evaporated under vacuum (140° C./0.1 mbar). A solid product is obtained with m.p. 176–183° C.

Analysis for $C_{242}H_{456}N_{54}$: Calculated: C=70.50%; H=11.15%; N=18.35%; Found: C=70.46%; H=11.17%; N=18.21%;

EXAMPLE 9

Preparation of the compound of the formula

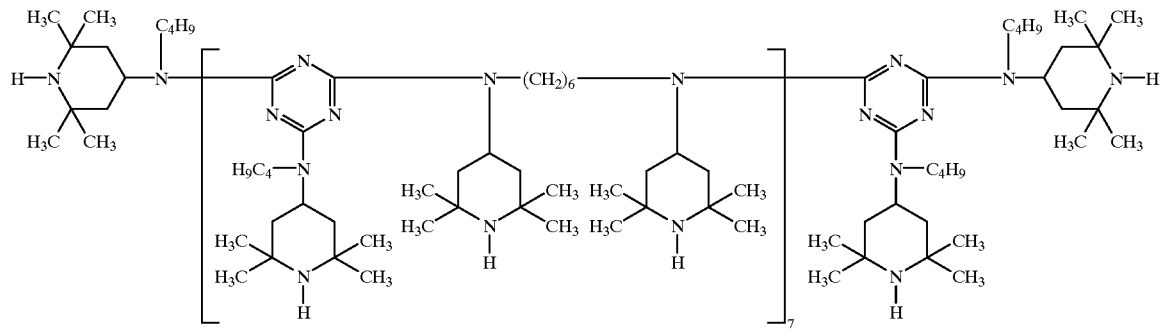

a) Preparation of the compound of the formula

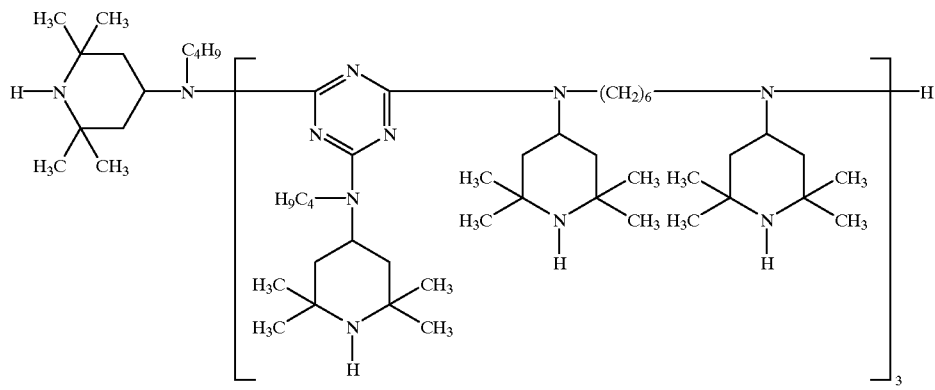

A solution of 8 g (0.005 moles) of the compound prepared as in Example 8 a) and 1.83 g (0.005 moles) of 2,4-dichloro-6-[(2,2,6,6-tetramethyl-4-piperidinyl)-butylamino]-[1,3,5]-triazine in 100 ml of xylene is heated to 40° C. for 1 hour.

After addition of 1.4 g (0.01 mole) of ground potassium carbonate, the mixture is heated to 60° C. for 2 hours and to 80° C. for 1 hour.

7.9 g (0.02 moles) of N,N'-bis(2,2,6,6-tetramethyl-4-piperidinyl)-1,6-hexanediamine and 0.4 g (0.01 mole) of ground sodium hydroxide are added and the mixture is heated to reflux for 4 hours being the reaction water eliminated off azeotropically.

The mixture is then filtered and the organic solution washed three times with ethylene glycol (30 ml) and with water (50 ml).

After drying on sodium sulfate and filtration, the organic solution is concentrated under vacuum (140° C./1 mbar).

After drying, a solid product with m.p. 143–147° C. is obtained.

Analysis for $C_{133}H_{253}N_{29}$: Calculated: C=70.73%; H=11.29%; N=17.98%; Found: C=70.68%; H=11.25%; N=17.88%;

b) Preparation of the above shown compound.

A solution of 9.5 g (0.0042 moles) of the compound prepared as in a) and 2.2 g (0.0021 moles) of the compound prepared as in Example 7 b) in 100 ml of trimethylbenzene is heated to reflux for 1 hour. 1.2 g (0.0084 moles) of ground potassium carbonate are added and the mixture is heated to reflux for 16 hours, being the reaction water eliminated off azeotropically.

The mixture is then concentrated to 50 ml raising the temperature up to 180° C. for further 10 hours.

Subsequently, the mixture is cooled, washed three times with water (30 ml) and dried on sodium sulfate.

After filtration, the organic solution is concentrated under vacuum (140° C./0.1 mbar).

After drying a solid product with m.p. 180–184° C. is obtained.

Analysis for $C_{322}H_{606}N_{72}$: Calculated: C=70.49%; H=11.13%; N=18.38%; Found: C=70.03%; H=11.01%; N=18.21%;

EXAMPLE 10

Preparation of the compound of the formula

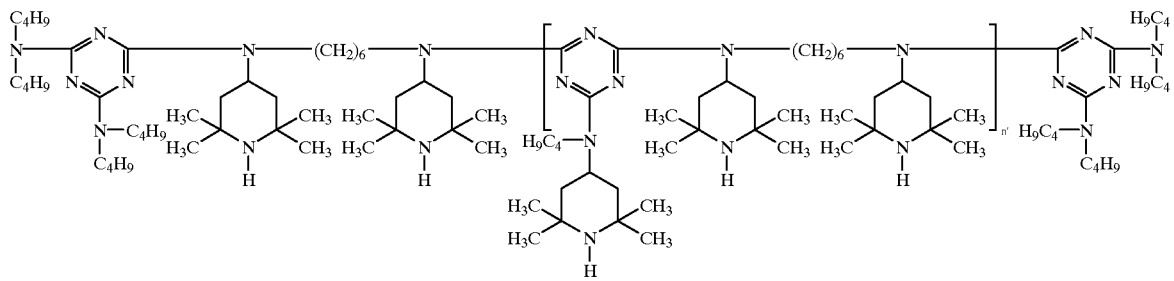

A solution of 74.3 g (0.35 moles) of N-(2,2,6,6-tetramethyl-4-piperidinyl)-n-butylamine in 50 ml of water is added slowly at 0° C. to a solution of 64.5 g (0.35 moles) of cyanuric chloride in 500 ml of xylene, keeping the temperature during the addition and for further 1 hour.

After 2 hours at room temperature, the mixture is cooled to 0° C. and an aqueous solution of 14.7 g (0.368 moles) of sodium hydroxide in 50 ml of water is added.

After ½ hour at 0° C. and for further 2 hours at room temperature, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour and 48.4 g (0.35 moles) of ground potassium carbonate are added and heated to 60° C. for 4 hours.

After washing with water, the organic phase is concentrated under vacuum at 60–70° C./10 mbar, being 250 ml of xylene recovered.

138.1 g (0.35 moles) of N,N'-bis(2,2,6,6-tetramethyl-4-piperidinyl)-1,6-hexanediamine are added and the mixture is heated to 150° C. for 2 hours, cooled again and added with 14 g (0.35 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 300 ml of xylene, filtered and washed three times with 100 ml of ethylene glycol.

After concentrating under vacuum at 60° C./10 mbar, 54.4 g (0.147 moles) of 2-chloro-4,6-bis-(dibutylamino)-1,3,5-triazine are added.

The mixture is heated to 140° C. for 3 hours and 20.3 g (0.147 moles) of ground potassium carbonate are added, being the mixture heated to reflux and being the reaction water eliminated off azeotropically.

The mixture is heated to 160° C. for 4 hours, added to further 20.3 g (0.147 moles) of ground potassium carbonate and heated again to 160° C. for 2 hours. After cooling to 60° C., the mixture is diluted with 300 ml of xylene, filtered and concentrated under vacuum at 140° C./1 mbar.

A solid is obtained with m.p.=130–136° C. after drying.

$\overline{Mn}$ (by GPC)=2830 g/mol $\overline{Mw}/\overline{Mn}$=1.22

Figure 8:
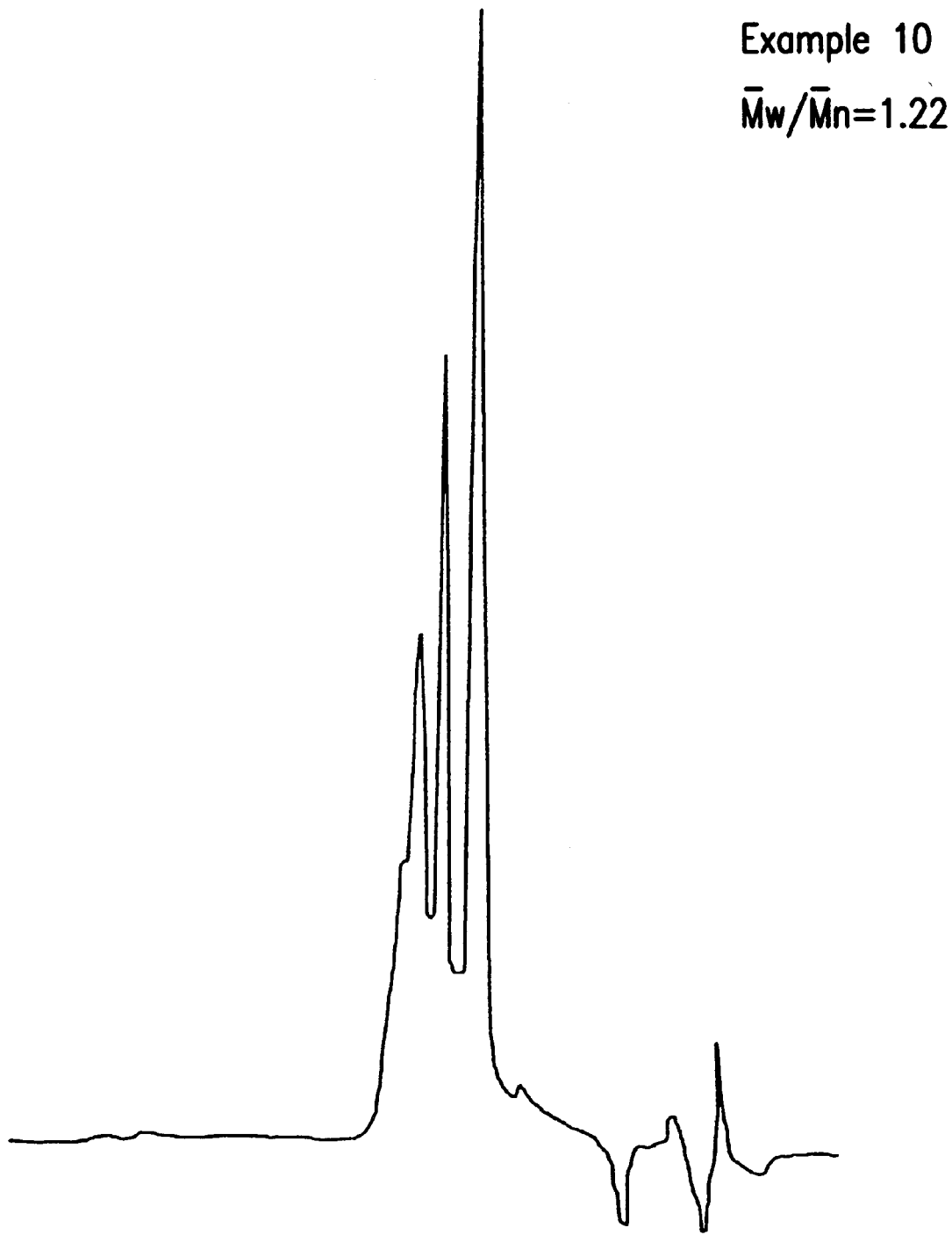

The GPC analysis shows a chromatogram as in FIG. 8.

EXAMPLE 11

Preparation of the compound of the formula

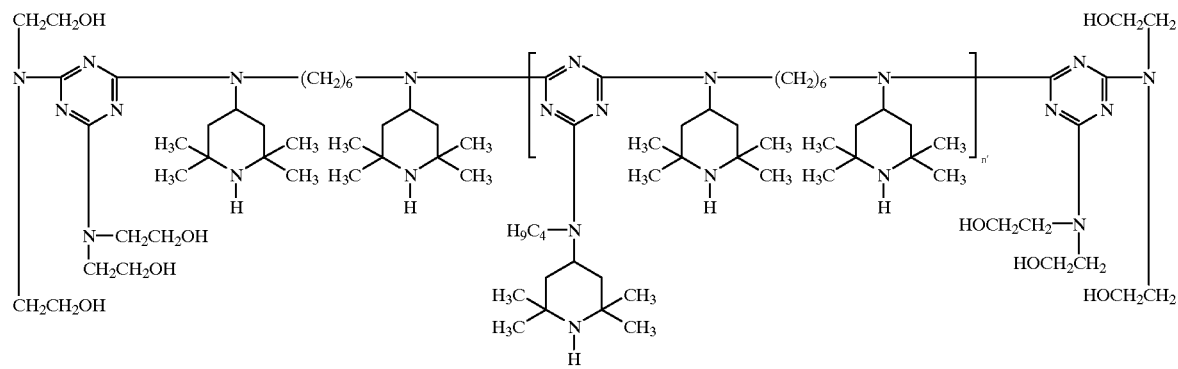

A) Synthesis of 2,4-bis-[bis-(2-hydroxyethyl)-amino]-6-chloro-[1,3,5]-triazine.

Keeping the temperature at 0–5° C., 92.2 g (0.5 moles) of cyanuric chloride are slowly added to a solution of 100 ml of acetone in 920 ml of water, cooled to 0° C. Subsequently, 105.1 g (1 mole) of diethanolamine are slowly added to the reaction mixture while maintaining the temperature at about 5° C.

The solution is stirred for ½ hour at 5–10° C. and a solution of 63.6 g (0.6 moles) of $Na_2CO_3$ in 700 ml of water is added slowly, being the solution heated to 45° C. and maintained at this temperature for 4 hours.

The mixture is then filtered and the solid so obtained is washed twice with water and dried in an oven under vacuum (100° C./1 mbar). After drying, the product is a white solid with a melting point of 146–147° C.

Analysis for $C_{11}H_{20}N_5O_4Cl$: Calculated: Cl=11.02%; Found: Cl=11.00%;

B) At 0° C., a solution of 74.3 g (0.35 moles) of N-(2,2,6,6-tetramethyl-4-piperidinyl)-n-butylamine in 50 ml of water is slowly added to a solution of 64.5 g (0.35 moles) of cyanuric chloride in 500 ml of xylene, keeping the temperature during the addition and for further 1 hour.

After 2 hours at room temperature, the mixture is cooled to 0° C. and an aqueous solution of 14.7 g (0.368 moles) of sodium hydroxide in 50 ml of water is added.

The organic phase is washed once with water, being the residual water eliminated off azeotropically.

After concentration under vacuum at 200° C./12.3 mbar, a yellowish product is obtained with a melting point of 155–160° C.

$\overline{Mn}$ (by GPC)=2852 g/mol
$\overline{Mw}/\overline{Mn}$=1.48

Figure 9:
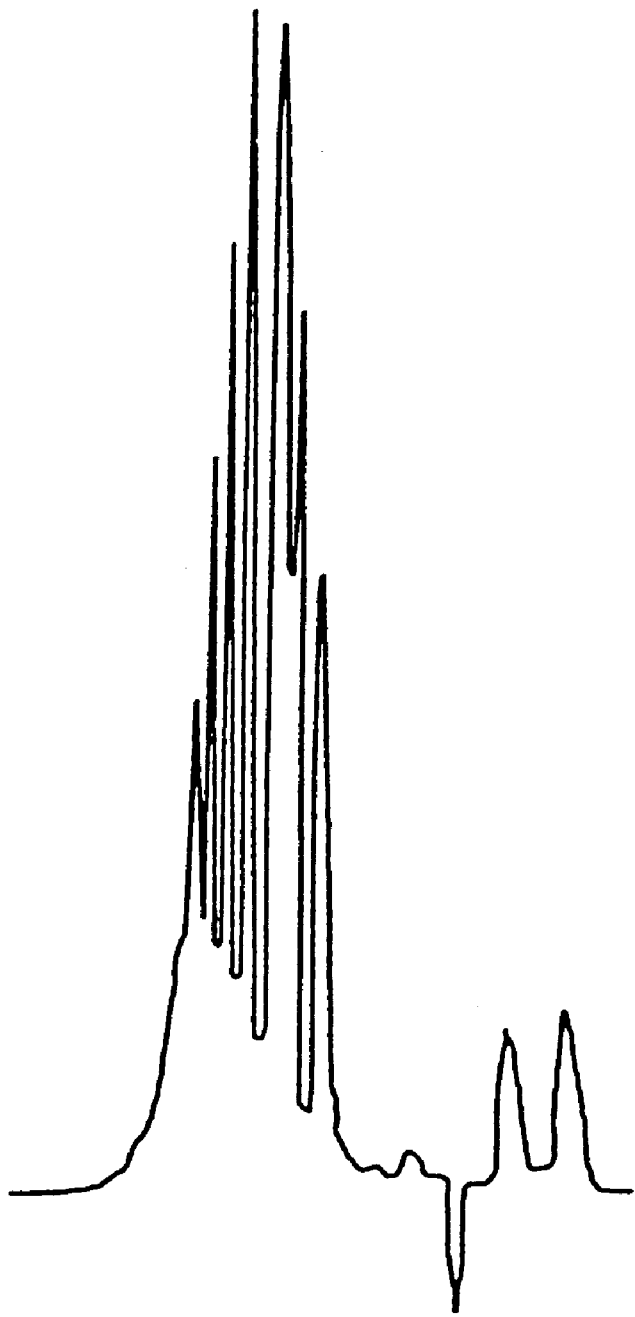

The GPO analysis shows a chromatogram as in FIG. 9.

EXAMPLE 12

Preparation of the compound of the formula

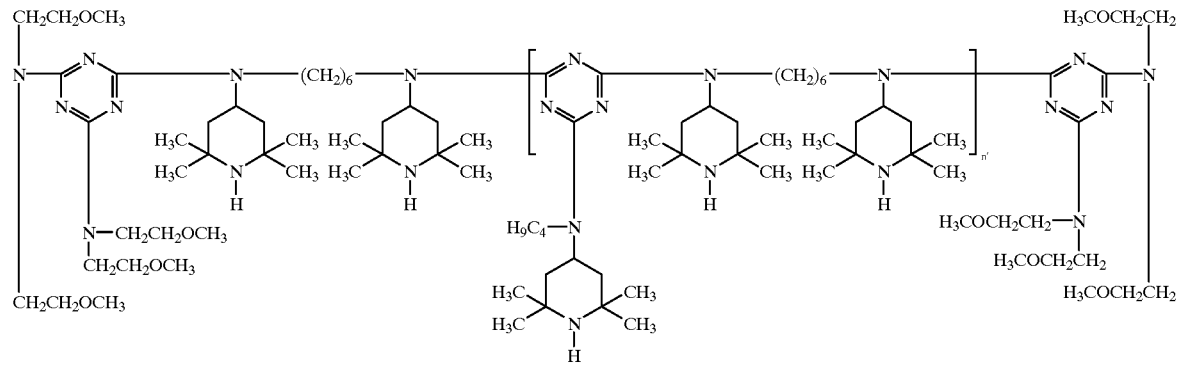

After ½ hour at 0° C. and further 2 hours at room temperature, the aqueous solution is separated off and 69.2 g (0.175 moles) of N,N'-bis-[2,2,6,6-tetramethyl-4-piperidinyl]-1,6-hexanediamine are added. The mixture is heated to 50° C. for 1 hour and 48.4 g (0.35 moles) of ground potassium carbonate are added and heated to 60° C. for 4 hours.

After washing with water, the organic phase is concentrated under vacuum at 60–70° C./10 mbar, being 250 ml of xylene recovered.

138.1 g (0.35 moles) of N,N'-bis-[2,2,6,6-tetramethyl-4-piperidinyl]-1,6-hexanediamine are added and the mixture is heated to 150° C. for 2 hours, cooled again and added with 14 g (0.35 moles) of ground sodium hydroxide.

The mixture is heated to 140° C. for 4 hours, being the residual water of reaction eliminated off azeotropically, and subsequently, the mixture is kept at 160° C. for further 4 hours.

After cooling to 60° C., the mixture is diluted with 300 ml of xylene, filtered and washed three times with 100 ml of ethylene glycol. After concentrating under vacuum at 60° C./10 mbar, 47.3 g (0.147 moles) of 2,4-bis-[bis-(2-hydroxyethyl)-amino]-6-chloro-[1,3,5]-triazine are added.

The mixture is heated to 140° C. for 10 hours, cooled to room temperature and added with 14 g (0.35 moles) of sodium hydroxide in 50 ml of water. The mixture is then heated to 95° C. for 4 hours, cooled to room temperature and the water phase is separated off.

A) Synthesis of 2,4-bis-[bis-(2-methoxyethyl)-amino]-6-chloro-[1,3,5]-triazine.

Following the procedure described in Example 11 under A), 92.2 g (0.5 moles) of cyanuric chloride are reacted with 133.2 g (1 mole) of bis-[2-methoxyethyl]-amine in a solution of 100 ml of acetone in 920 ml of water.

After evaporation of the acetone/water mixture, a resinous compound is obtained which is crystallized by ethanol. The product is a white solid with a melting point of 40–44° C.

Analysis for $C_{15}H_{28}N_5O_4Cl$: Calculated: Cl=9.38%; Found: Cl=9.42%;

B) Following the procedure described in Example 11 under B) and using the appropriate amounts of the suitable reactants, the desired product is obtained as a white solid with a melting point of 138–153° C.

$\overline{Mn}$ (by GPC)=3017 g/mol
$\overline{Mw}/\overline{Mn}$=1.35

Figure 10:
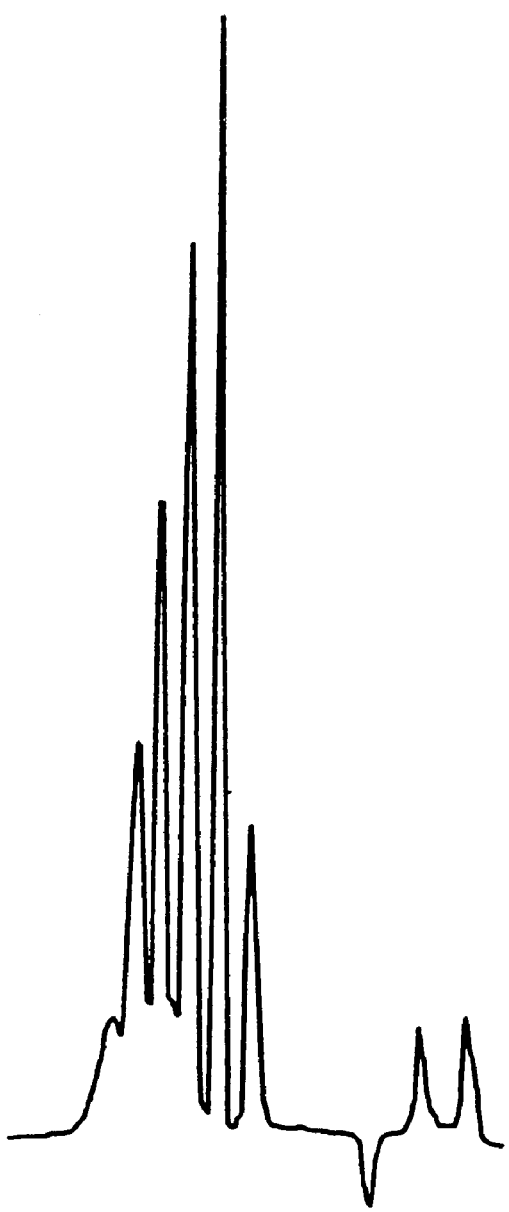

The GPC analysis shows a chromatogram as in FIG. 10.

EXAMPLE D

Preparation of the compound of the formula

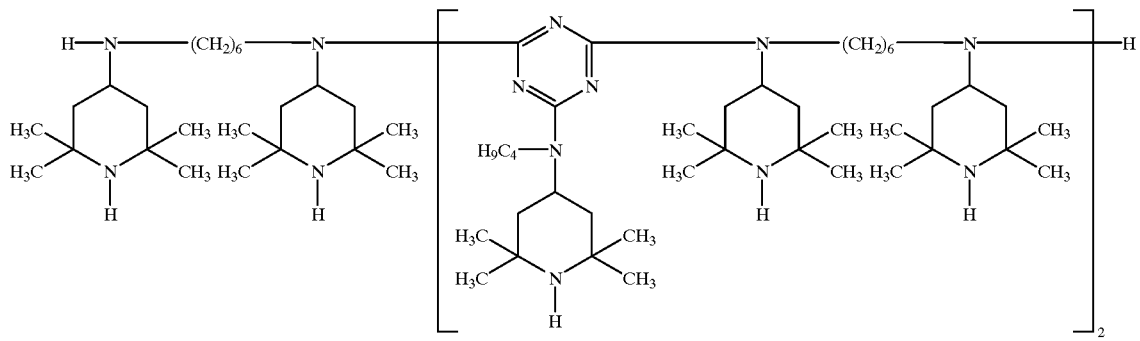

At 0° C., a solution of 74.3 g (0.35 moles) of N-(2,2,6,6-tetramethyl-4-piperidinyl)-n-butylamine in 50 ml of water is added slowly and under stirring to a solution of 64.5 g (0.35 moles) of cyanuric chloride in 500 ml of xylene. The mixture is then stirred during 2 hours at room temperature and, after cooling to 0° C., an aqueous solution of 14.7 g (0.368 moles) of sodium hydroxide in 50 ml of water is added. Subsequently, the aqueous solution is separated off and 69.2 g (0.175 moles) of N,N'-bis-[2,2,6,6-tetramethyl-4-piperidinyl]-1,6-hexanediamine are added. The mixture is heated to 50° C. for 1 hour. Then, 48.4 g (0.35 moles) of ground anhydrous potassium carbonate are added and the mixture is heated to 60° C. for 4 hours. After washing with water, the organic phase is concentrated a little (250 ml of xylene are recovered) and 1381 g (3.5 moles) of N,N'-bis-[2,2,6,6-tetramethyl-4-piperidinyl]-1,6-hexanediamine are added. After heating the mixture to 140° C. for 2 hours, 28 g (0.70 moles) of ground sodium hydroxide are added and the mixture is heated to reflux for 8 hours, being the water of the reaction distilled off azeotropically. 250 ml of xylene are added and the mixture is then filtered. The solution is concentrated under vacuum (140° C./1 mbar) and the excess of N,N'-bis-[2,2,6,6-tetramethyl-4-piperidinyl]-1,6-hexanediamine is eliminated off under vacuum (190° C./0.2 mbar). The solid so obtained is dissolved in xylene, washed four times with water (50 ml) and dried on $Na_2SO_4$. After filtration, the xylene solution is evaporated under vacuum (140° C./10 mbar) and, after drying, a product with a melting point of 130–138° C. is obtained.

Analysis for $C_{104}H_{200}N_{22}$: Calculated: C=71.02%; H=11.46%; N=17.52%; Found: C=70.95%; H=11.48%; N=17.54%;

EXAMPLE D-1

Preparation of the compound of the formula

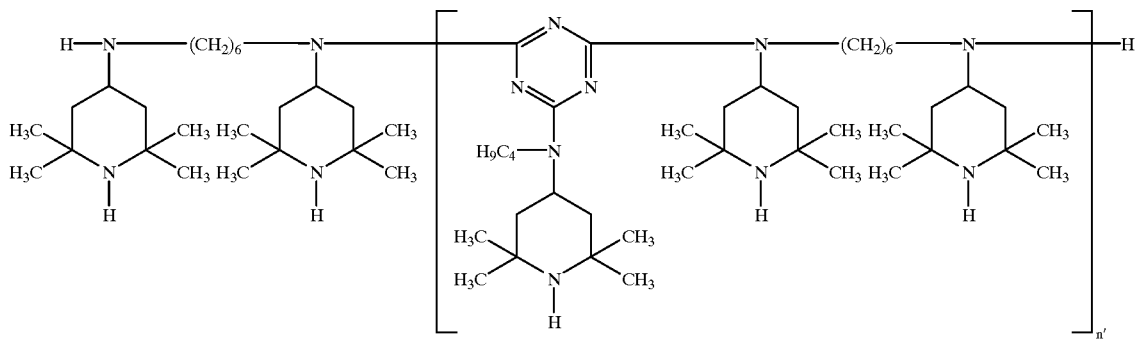

At 0° C., a solution of 74.3 g (0.35 moles) of N-(2,2,6,6-tetramethyl-4-piperidinyl)-n-butylamine in 50 ml of water is added slowly and under stirring to a solution of 64.5 g (0.35 moles) of cyanuric chloride in 500 ml of xylene. The mixture is then stirred 2 hours at room temperature and, after cooling to 0° C., added with an aqueous solution of 14.7 g (0.368 moles) of sodium hydroxide in 50 ml of water. Subsequently, the aqueous solution is separated off and 69.2 g (0.175 moles) of N,N'-bis-[2,2,6,6-tetramethyl-4-piperidinyl]-1,6-hexanediamine are added. The mixture is heated to 50° C. for 1 hour. Then, 48.4 g (0.35 moles) of ground anhydrous potassium carbonate are added and the mixture is heated to 60° C. for 4 hours.

After washing with water, the organic phase is concentrated a little (250 ml of xylene are recovered) and 138.1 g (0.35 moles) of N,N'-bis-[2,2,6,6-tetramethyl-4-piperidinyl]-1,6-hexanediamine are added.

After heating the mixture to 140° C. for 2 hours, 28 g (0.70 moles) of ground sodium hydroxide are added and the mixture is heated to reflux for 8 hours, being the water of the reaction distilled off azeotropically.

The mixture is then cooled to 60° C., diluted with 300 ml of xylene and filtered. Subsequently, the solution is washed three times with 100 ml of ethylene glycol and concentrated under vacuum at 140° C./1 mbar. After drying, the solid obtained has a melting point of 138–143° C.

$\overline{Mn}$ (by GPC)=2555 g/mol $\overline{Mw}/\overline{Mn}$=1.25

Figure 11:
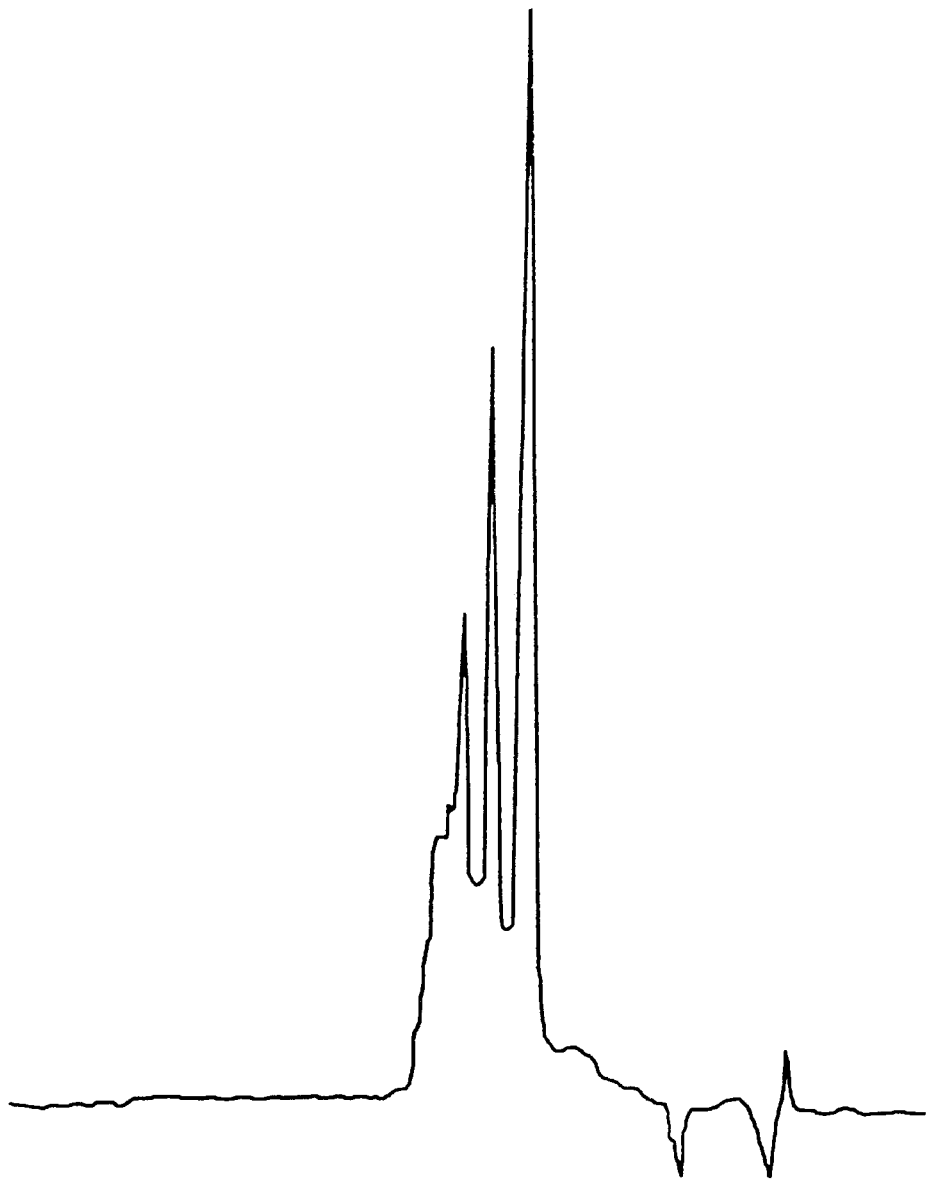
Figure 12:
Figure 13:
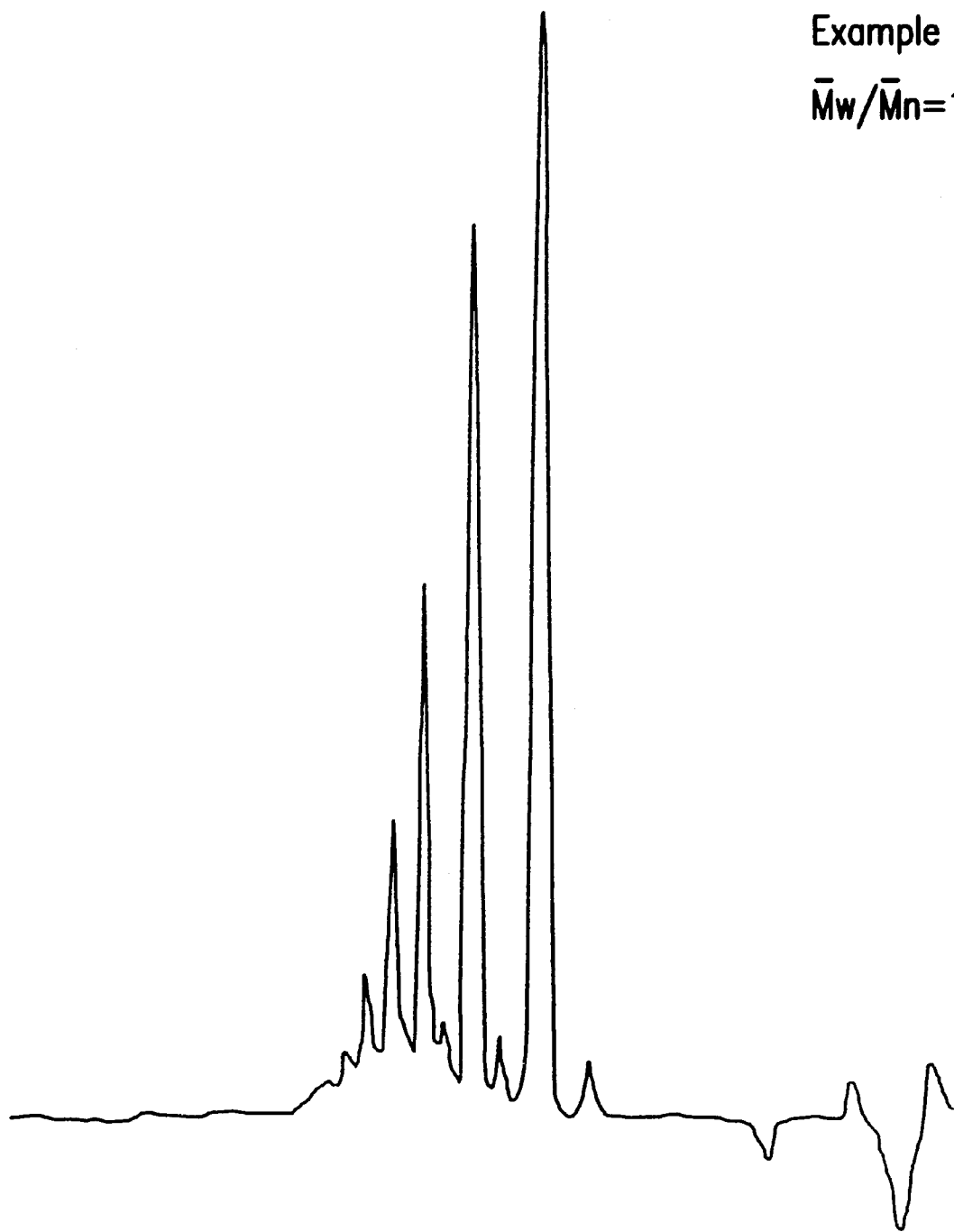
Figure 14:
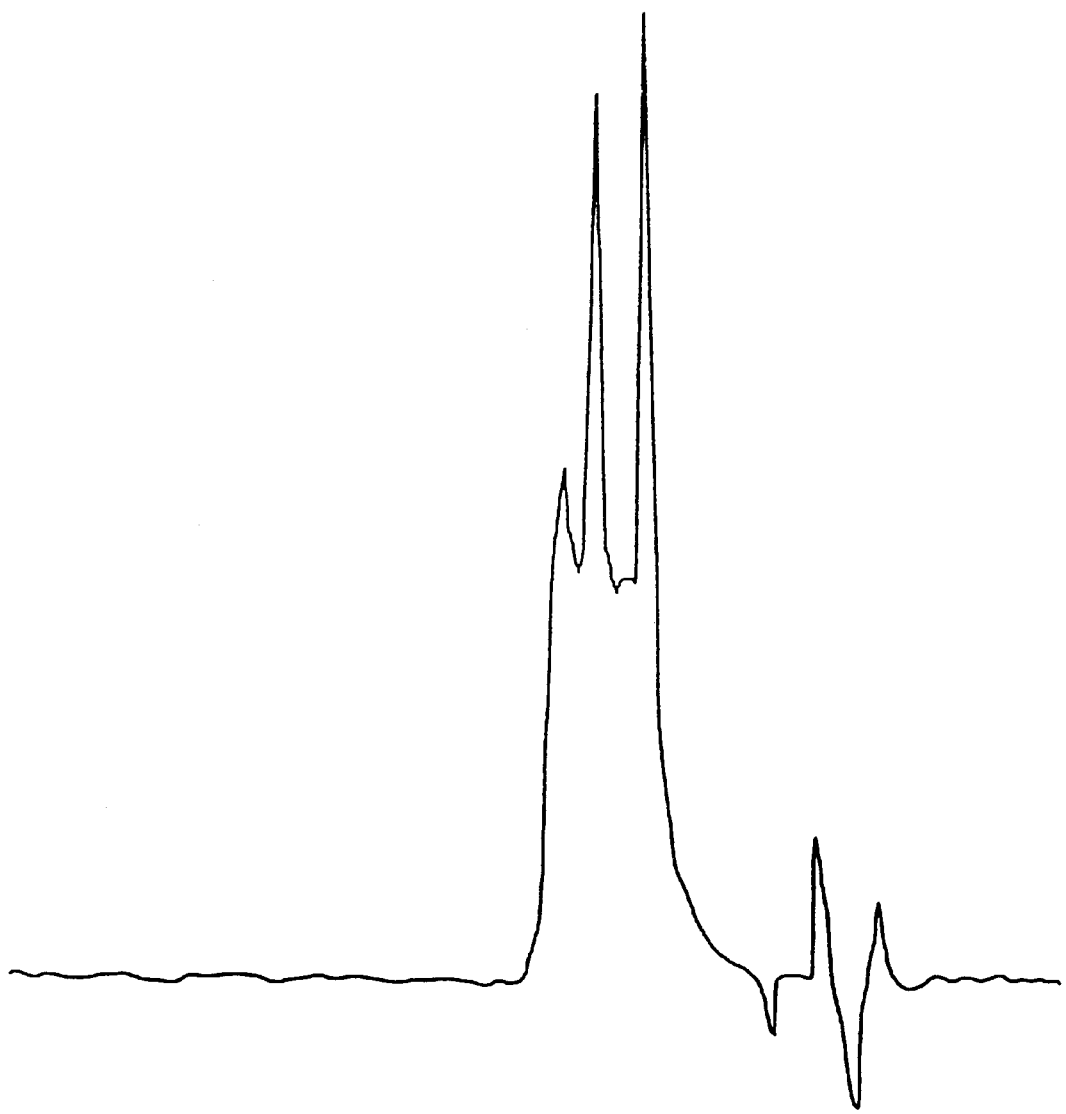
Figure 15:
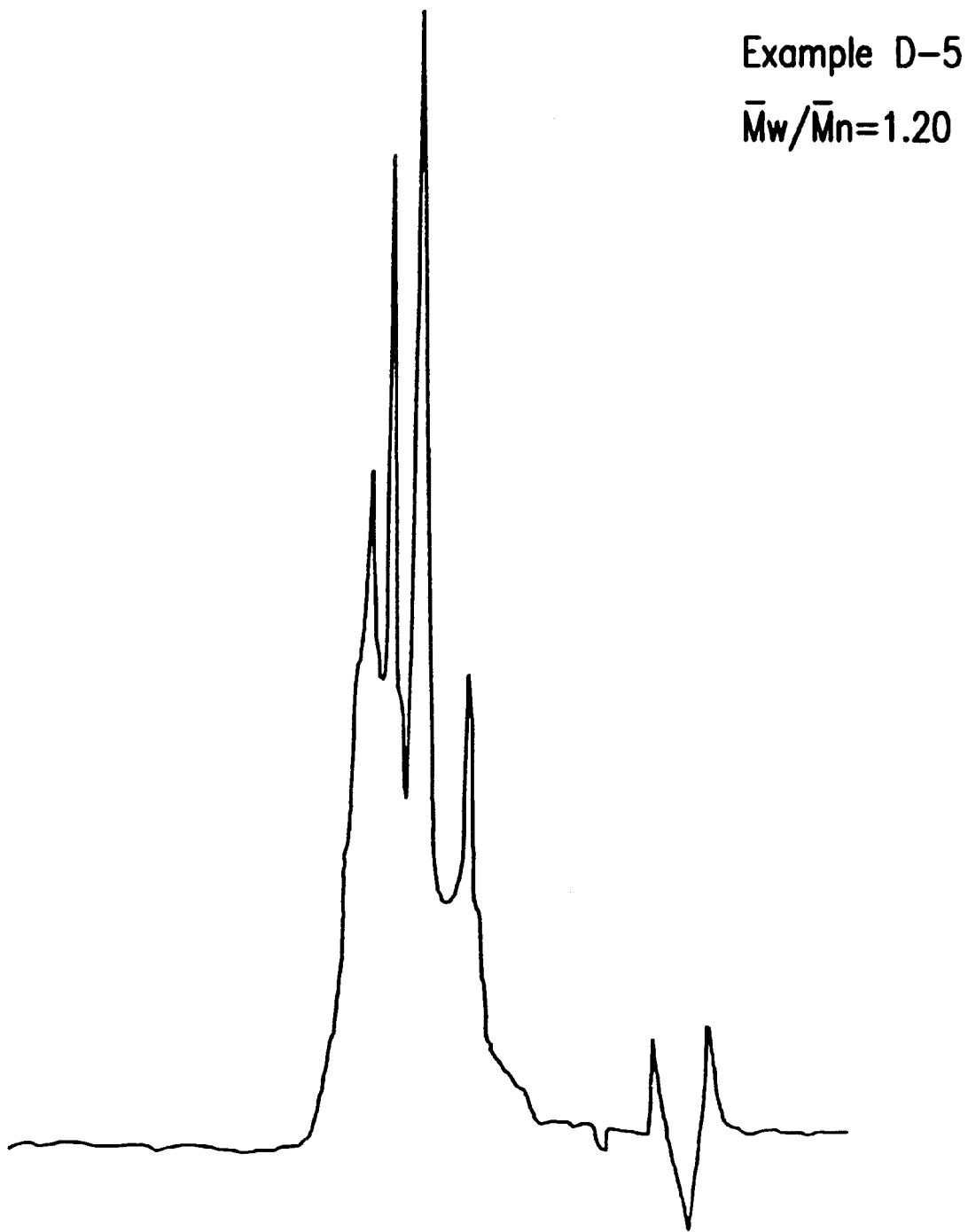

The GPC analysis shows a chromatogram as in FIG. 11.

EXAMPLES D-2 to D-5

Following the process described in Example D-1 and using the respective reagents in the appropriate molar ratios, the following compounds of formula The mixtures are extruded at 200–230° C. to obtain polymer granules which are then converted into fibres using a pilot-type apparatus (®Leonard-Sumirago(VA), Italy) and operating under the following conditions:

Extruder temperature: 230–245° C.
Head temperature: 255–260° C.
Draw ratio: 1:3.5
Linear density: 11 dtex per filament The fibres prepared in this way are exposed, after mounting on white cardboard, in a 65WR Weather-O-Meter (ASTM D2565-85) with a black panel temperature of 63° C.

For samples taken after various times of exposure to the light, the residual tenacity is measured using a constant-speed tensometer, and the exposure time in hours needed to halve the initial tenacity ($T_{50}$) is then calculated.

For purposes of comparison, fibres prepared under the same conditions as stated above, but without adding the stabilizers of the present invention, are also exposed.

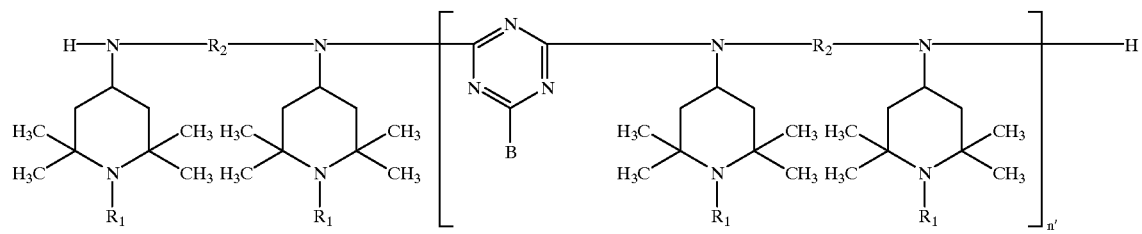

are prepared.

| Example | $R_1$ | $R_2$ | B | melting point (° C.) | $\overline{Mn}$ | $\overline{Mw}/\overline{Mn}$ |
|---|---|---|---|---|---|---|
| D-2 | —H | —(CH$_2$)$_6$— | H$_3$C—C(CH$_3$)$_2$—CH$_2$—C(CH$_3$)$_2$—NH— | 97–105 | 2631 | 1.28 |
| D-3 | —H | —(CH$_2$)$_6$— | H$_3$C—C(CH$_3$)$_2$—NH— | 121–128 | 2475 | 1.34 |
| D-4 | —H | —(CH$_2$)$_6$— | morpholino (N—O ring) | 125–130 | 2340 | 1.24 |
| D-5 | —H | —(CH$_2$)$_6$— | —N(C$_4$H$_9$)$_2$ | 68–72 | 2773 | 1.20 |

The GPC analysis of Examples 12 to 15 shows a chromatogram as in FIGS. D-2 to D-5.

EXAMPLE I

Light-stabilizing action in polypropylene fibres.

2.5 g of the stabilizer shown in Table 1,1 g of tris(2,4-di-t-butylphenyl) phosphite, 1 g of calcium monoethyl 3,5-di-t-butyl-4-hydroxybenzyl-phosphonate, 1 g of calcium stearate and 2.5 g of titanium dioxide are mixed in a slow mixer with 1000 g of polypropylene powder having a melt index=12 g/10 min (measured at 230° C. and 2.16 kg).

The results are shown in Table 1.

TABLE 1

| Stabilizer | $T_{50}$ (hours) |
|---|---|
| without stabilizer | 250 |
| compound of Example 1 | 2100 |
| compound of Example 2 | 1950 |
| compound of Example 3 | 1990 |
| compound of Example 4 | 1820 |

TABLE 1-continued

| Stabilizer | $T_{50}$ (hours) |
|---|---|
| compound of Example 5 | 1900 |
| compound of Example 10 | 2210 |

EXAMPLE II

Pigment interaction in polypropylene plaques.

5.625 g of the stabilizer shown in Table 2, 13.500 g of Pigment Blue 15 "Flush" (50% mixture in polyethylene) and 25.875 g of polypropylene powder (having a melt index of approximately 14 measured at 230° C. and 2.16 Kg) are added to fill a ®Haake internal mixer at room temperature (Haake Buchler Rheochord System 40 using a 60 cc 3 piece Rheomixer with cam blades). The cam blades are rotating at 5 RPM (revolutions per minute). A ram closed the bowl under a weight of 5 kg. The temperature is increased to 180° C. and held at 180° C. The total time is 30 minutes.

The mixture is removed while at 180° C. after 30 minutes and cooled down to room temperature. The mixture so obtained—called the "concentrate"—will be used again.

0.900 g of this concentrate, 3.600 g of titanium dioxide "Flush" (50% mixture in polyethylene), and 40.500 g of polypropylene powder (having a melt index of approximately 14 measured at 230° C. and 2.16 Kg) are added to a ®HAAKE mixer bowl at 160° C. The cam blades are rotating at 20 RPM. A ram closes the bowl under a weight of 5 kg. The temperature is increased to 170° C. and the RPM is increased to 125. The total time is 30 minutes.

The molten mixture is removed at 170° C., transferred to a hand held tool at room temperature and transformed into a round plaque 1 mm×25 mm in diameter. The mixture now so obtained is called the "letdown" and the plaque the "letdown plaque."

Color difference, delta E (CIE color difference equation), of sample letdown plaque containing the stabilizer indicated in Table 2 versus control letdown plaque without the stabilizer are measured. The measurement is done using an Applied Color Systems Spectrophotometer Model CS-5 (USA). The measurement parameters used are 400–700 nm—scan, small area view, reflectance, illuminate D65, 10 degree observer.

The above processing conditions are designed to simulate the manufacture of concentrates (masterbatches) of pigments and stabilizers and the subsequent let-down (dilution) into finished plastic articles.

A high delta E indicates pigment agglomeration and poor dispersion. A delta E of 0.5 or less will not be seen as different by the eye.

TABLE 2

| Stabilizer | Delta E |
|---|---|
| compound of Example 1 | 0.3 |
| compound of Example 10 | 0.4 |

EXAMPLE III

Light-stabilizing action in polypropylene tapes.

1 g of each of the compounds listed in Table 3, 1 g of tris[2,4-di-tert-butylphenyl] phosphite, 0.5 g of pentaerythritol tetrakis[3-(3,5-di-tert-butyl-4-hydroxyphenyl) propionate] and 1 g of calcium stearate are mixed in a turbomixer with 1000 g of polypropylene powder having a melt index of 2.1 (measured at 230° C. and 2.16 Kg).

The mixtures are extruded at 200–220° C. to give polymer granules which are subsequently converted to stretched tapes of 50 µm thickness and 2.5 mm width, using a semi-industrial type of apparatus (®Leonard-Sumirago (VA)—Italy) and working under the following conditions:
Extruder temperature: 210–230° C.
Head temperature: 240–260° C.
Stretch ratio: 1:6

The tapes thus prepared are mounted on a white card and exposed in a Weather-O-Meter 65 WR (ASTM D 2565–85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed.

The results obtained are shown in Table 3.

TABLE 3

| Stabilizer | $T_{50}$ (hours) |
|---|---|
| without stabilizer | 500 |
| compound of Example 1 | 2920 |
| compound of Example 10 | 2600 |

EXAMPLE IV

Antioxidant action in polypropylene plaques.

1 g of each of the compounds listed in Table 4 and 1 g of calcium stearate are mixed in a slow mixer with 1000 g of polypropylene powder having a melt index of 4.3 (measured at 230° C. and 2.16 Kg).

The mixtures are extruded twice at 200–220° C. to give polymer granules which are then converted into plaques of 1 mm thickness by compression-moulding at 230° C. for 6 minutes.

The plaques are then punched using a DIN 53451 mould and the specimens obtained are exposed in a forced circulation air oven maintained at a temperature of 135° C.

The specimens are checked at regular intervals by folding them by 180° in order to determine the time (in hours) required for fracturing them.

The results obtained are given in Table 4.

TABLE 4

| Stabilizer | Time to fracture (hours) |
|---|---|
| without stabilizer | 250 |
| compound of Example 1 | 1560 |
| compound of Example 10 | 1490 |

EXAMPLE V

Color of polypropylene plaques after oven ageing.

5 g of each of the compounds listed in Table 5, 1 g of tris[2,4-di-tert-butylphenyl] phosphite, 1 g of pentaerythritol tetrakis[3-(3,5-di-tert-butyl-4-hydroxyphenyl) propionate] and 1 g of calcium stearate are mixed in a slow mixer with 1000 g of polypropylene powder having a melt index of 2.1 (measured at 230° C. and 2.16 Kg).

The mixtures are extruded twice at 200–220° C. to give polymer granules which are then converted into plaques of 1 mm thickness by compression-moulding at 230° C. for 6 minutes.

The plaques are then exposed for seven days in a forced circulation air oven maintained at 120° C. After the oven exposure, the yellowness index (YI) of the plaques is measured according to ASTM D 1925 by ®MINOLTA CR 210 chromometer (MINOLTA—Japan). The results obtained are shown in Table 5.

TABLE 5

| Stabilizer | YI |
|---|---|
| compound of Example 1 | 22.10 |
| compound of Example 10 | 21.10 |

We claim:

1. A mixture containing at least three different compounds of formula (I)

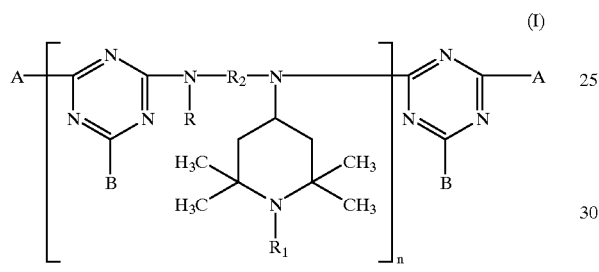

(I)

in which;

n is 3, 4, 5, 6, 7, 8, 9, 10, 11, 12, 13, 14 or 15;

the radicals $R_1$ are independently of one another hydrogen, $C_1$–$C_8$alkyl, $C_2$–$C_8$hydroxyalkyl, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below except hydrogen;

or $R_2$ is a group of the formula (a), (b) or (c);

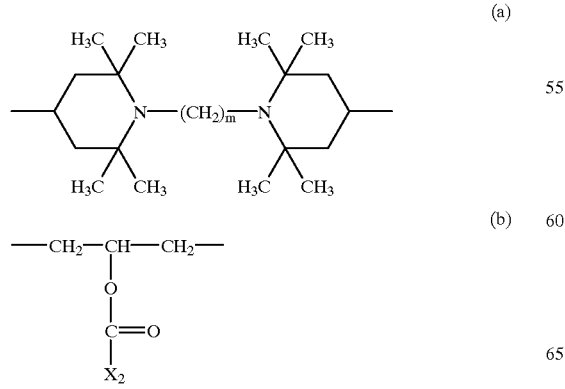

(a)

(b)

-continued

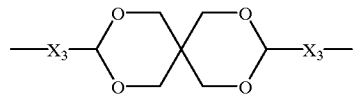

(c)

with m being 2 or 3, $X_2$ being $C_1$–$C_{18}$alkyl, $C_5$–$C_{12}$cycloalkyl which is unsubsubtuted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_3$, —$N(R_4)(R_5)$ or a group of the formula (II);

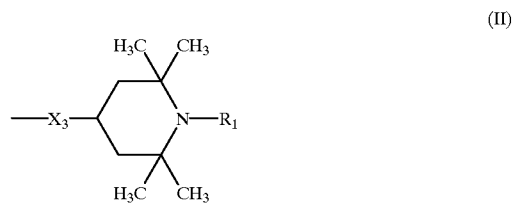

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1C_4$alkyl or $C_1C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

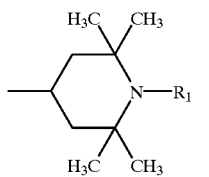

(IV)

or $C_2$–$C_4$alkyl which is substituted in the 2, 3 or 4 position by —OH, $C_1$–$C_8$alkoxy, di($C_1$–$C_4$alkyl)amino or a group of the formula (III);

R has one of the definitions given for $R_6$; and the radicals B have independently of one another one of the definitions given for A;

with the proviso that in the individual recurrent units of formula (I), each of the radicals B, R, $R_1$ and $R_2$ has the same or a different meaning, and which vary only by the variable n, said mixture having a polydispersity $\overline{M}w/\overline{M}n$ of 1.1 to 1.7.

2. A mixture according to claim 1 where in the compound of formula (I), R is a group of the formula (IV).

3. A mixture according to claim 1 where in the compound of formula (I), n is 3, 4, 5, 6, 7, 8, 9, 10, 11, 12 or 13;

the radicals $R_1$ are independently of one another hydrogen, $C_1$–$C_8$alkyl, —$CH_2CN$, $C_3$–$C_6$alkenyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

$R_6$ is hydrogen, $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV) or $C_2$–$C_4$alkyl which is substituted in the 2, 3 or 4 position by —OH, $C_1$–$C_8$alkoxy, di($C_1$–$C_4$alkyl)amino or a group of the formula (III); and R is a group of the formula (IV).

4. A mixture according to claim 1 where in the compound of formula (I), the radicals $R_1$ are independently of one another hydrogen, $C_1$–$C_4$alkyl, allyl, benzyl or acetyl.

5. A mixture according to claim 1 where in the compound of formula (I), n is 3, 5 or 7.

6. A mixture according to claim 1 where in the compound of formula (I), $R_2$ is $C_2$–$C_{10}$alkylene, cyclohexylene, cyclohexylenedi($C_1$–$C_4$alkylene), $C_1$–$C_4$alkylenedicyclohexylene or phenylenedi($C_1$–$C_4$alkylene);

$R_3$, $R_4$ and $R_5$, which are identical or different, are hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (III); or —$N(R_4)(R_5)$ is additionally a group of the formula (III); and $R_6$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (IV) or $C_2$–$C_3$alkyl which is substituted in the 2 or 3 position by —OH, $C_1$–$C_4$alkoxy, di($C_1$–$C_4$alkyl)amino or a group of the formula (III).

7. A mixture according to claim 1 where in the compound of formula (I), $R_2$ is $C_2$–$C_8$alkylene;

$R_3$, $R_4$ and $R_5$, which are identical or different, are hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or —$N(R_4)(R_5)$ is additionally 4-morpholinyl; and $R_6$ is hydrogen, $C_1$–$C_8$alkyl, cyclohexyl which is unsubstituted or substituted by methyl; benzyl, tetrahydrofurfuryl, a group of the formula (IV) or $C_2$–$C_3$alkyl substituted in the 2 or 3 position by —OH, $C_1$–$C_4$alkoxy, dimethylamino, diethylamino or 4-morpholinyl.

8. A mixture according to claim 1 where in the compound of formula (I), n is 3, 5 or 7;

the radicals $R_1$ are independently of one another hydrogen or methyl;

$R_2$ is $C_2$–$C_6$alkylene;

the radicals A are independently of one another —$N(R_4)(R_5)$ or a group of the formula (II);

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

X is >$NR_6$;

$R_6$ is $C_1$–$C_4$alkyl; and the radicals B have independently of one another one of the definitions given for A.

9. A mixture according to claim 1 where the compound of formula (I) corresponds to a compound of formula (X)

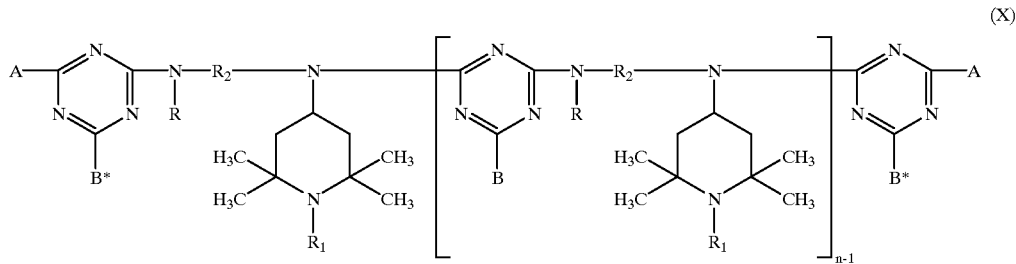

wherein n, A, B, R, $R_1$ and $R_2$ are as defined in claim 1 and B* has one of the definitions given for B;

with the provisos that (1) B* is different from B and (2) each of the radicals B, R, $R_1$ and $R_2$ has the same meaning in the individual recurring units of the formula.

10. A mixture according to claim 1, said mixture having a polydispersity $\overline{M}w/\overline{M}n$ of 1.1 to 1.6.

11. A mixture according to claim 1, said mixture having a polydispersity $\overline{M}w/\overline{M}n$ of 1.1 to 1.5.

12. A mixture according to claim 1, said mixture having a polydispersity $\overline{M}w/\overline{M}n$ of 1.1 to 1.4.

13. A mixture according to claim 1, containing a) a compound of formula (Ia)

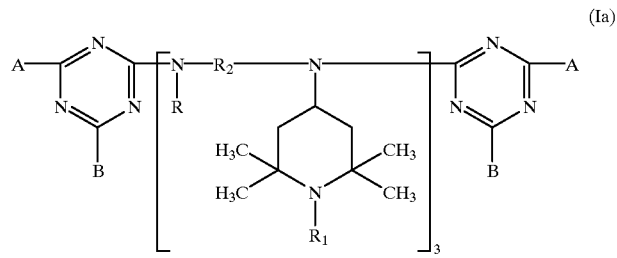

b) a compound of formula (Ib), and

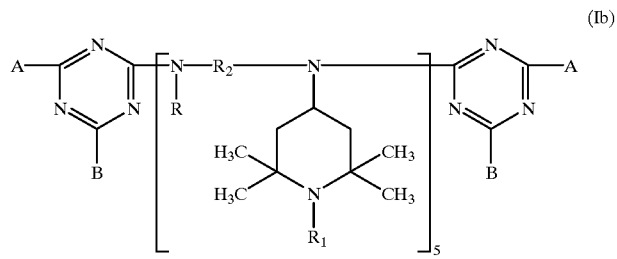

c) a compound of formula (Ic)

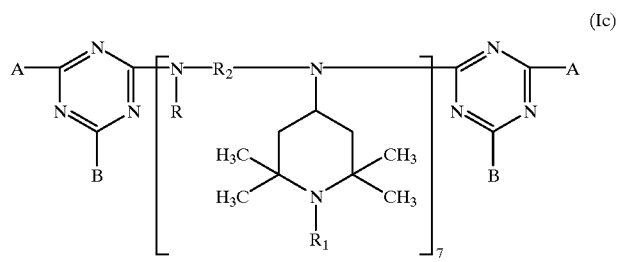

wherein A, B, R, $R_1$ and $R_2$ are in the formulas (Ia), (Ib) and (Ic) identical and are as defined in claim 1, and the ratio of the compounds of formulas (Ia) to (Ib) to (Ic) is 2:1.5:1 to 2:0.5:0.05.

14. A mixture according to claim 13 wherein the ratio of the compounds of formulas (Ia) to (Ib) to (Ic) is 2:1:0.5 to 2:0.5:0.08.

15. A mixture according to claim 13 wherein the ratio of the compounds of formulas (Ia) to (Ib) to (Ic) is 2:0.75:0.3 to 2:0.5:0.08.

16. A mixture according to claim 13 wherein the radicals $R_1$ are independently of one another hydrogen or methyl;

$R_2$ is $C_2$–$C_6$alkylene;

A and B which are identical or different, are —$N(R_4)(R_5)$ or a group of formula (II) with $R_1$ being as defined above;

$R_4$ and $R_5$, which are identical or different, are hydrogen, $C_1$–$C_8$alkyl, 2-hydroxyethyl or 2-methoxyethyl, or —$N(R_4)(R_5)$ is additionally 4-morpholinyl;

X is >$NR_6$;

$R_6$ is $C_1$–$C_4$alkyl; and

R is a group of forrnula (IV) with $R_1$ being defined above.

17. A method for preparing a mixture according to claim 1, which comprises 1) reacting a compound of the formula (A)

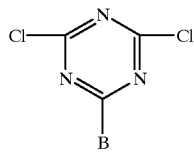

(A)

with a compound of the formula (B)

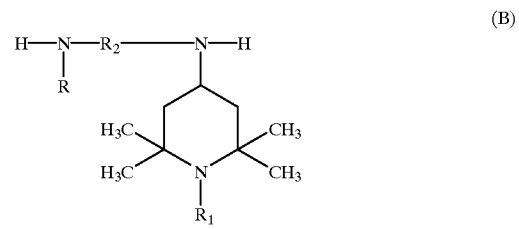

(B)

in a stoichiometric ratio to obtain a compound of the formula (C);

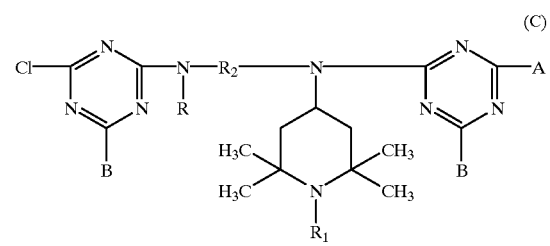

(C)

2) reacting a compound of the formula (C) with a compound of the formula (B) in a ratio of 1:2 to 1:3, to obtain a mixture of at least three different compounds of the formula (D) with n being 3, 4, 5, 6, 7, 8, 9, 10, 11, 12, 13, 14 or 15;

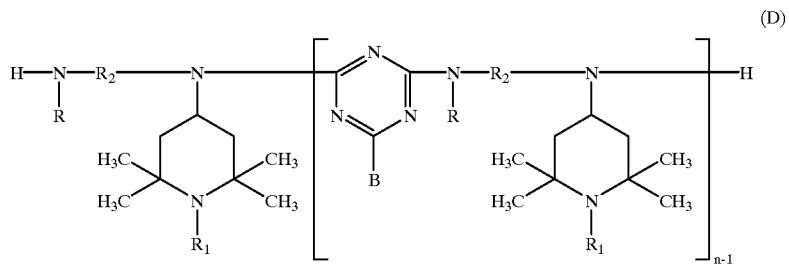

(D)

3) reacting the mixture obtained in 2) with a compound of the formula (E)

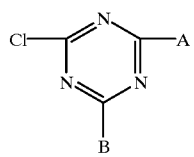

(E)

in a stoichiometric ratio to obtain a mixture as defined in claim 1, the reactions 1) to 3) being carried out in an organic solvent in the presence of an inorganic base.

18. A method according to claim 17, wherein the ratio of the compound of formula (C) to the compound of formula (B) is 1:2 and n is 3, 5 and 7.

19. A mixture according to claim 9 wherein the compounds of formula (I) correspond to compounds of formula (X).

20. A mixture according to claim 1 wherein the three different compounds of formula (I) correspond to compounds of formulas (Xa), (Xb) and (Xc)

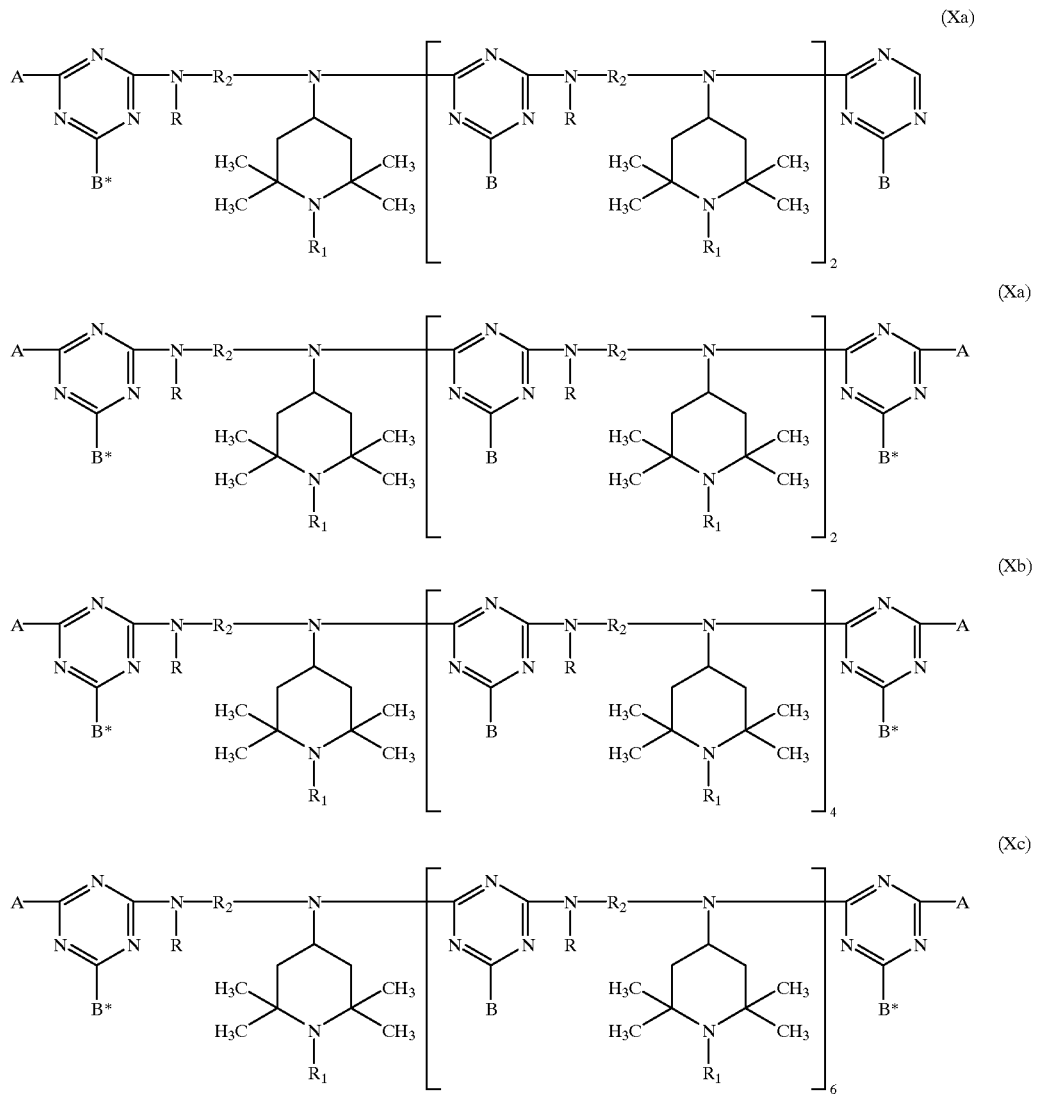

wherein
the radicals $R_1$ are independently of one another hydrogen or methyl;

$R_2$ is $C_2$–$C_6$alkylene;

A and B*, which are identical or different, are —$N(R_4)(R_5)$ or a group of the formula (II);

$R_4$ and $R_5$, which are identical or different, are hydrogen, $C_1$–$C_8$alkyl, 2-hydroxyethyl or 2-methoxyethyl or —$N(R_4)(R_5)$ is additionally 4-morpholinyl;

B is a group of the formula (II) with $R_1$ being as defined above;

X is >$NR_6$;

$R_6$ is $C_1$–$C_4$alkyl; and

R is a group of the formula (IV) with $R_1$ being as defined above;

with the proviso that each of the radicals B, R, $R_1$ and $R_2$ has the same meaning in the individual recurring units of the formulae.

21. A mixture according to claim 20, wherein A and B*, which are identical or different, are —$N(C_1$–$C_8$alkyl$)_2$ or a group

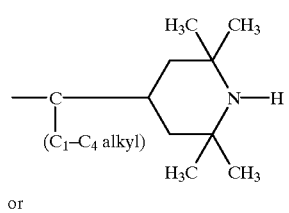

or

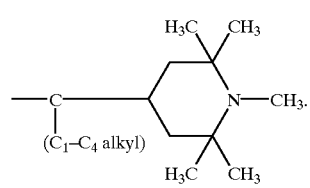

22. A mixture according to claim 20, wherein $R_1$ is hydrogen, $R_2$ is hexamethylene, A and B* are dibutylamino, B is N-(2,2,6,6-tetramethyl-4-piperidinyl)-butylamino and R is 2,2,6,6-tetramethyl-4-piperidinyl.

23. A mixture according to claim 20 wherein the ratio of the compounds of formulas (Xa) to (Xb) to (Xc) is 2:1.5:1 to 2:0.5:0.05.

24. A mixture according to claim 20 wherein the ratio of the compounds of formulas (Xa) to (Xb) to (Xc) is 2:1:0.5 to 2:0.5:0.08.

25. A mixture according to claim 20 wherein the ratio of the compounds of formulas (Xa) to (Xb) to (Xc) is 2:0.75:0.3 to 1:0.5:0.08.

26. A method according to claim 17, wherein the compound of formula (E) is a compound of formula (E*)

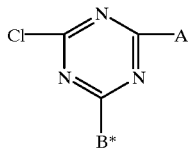

(E*)

wherein

B* has one of the definitions given for B; with the proviso that B* is different from B in step 2.

27. A mixture containing at least three different compounds of formula (I)

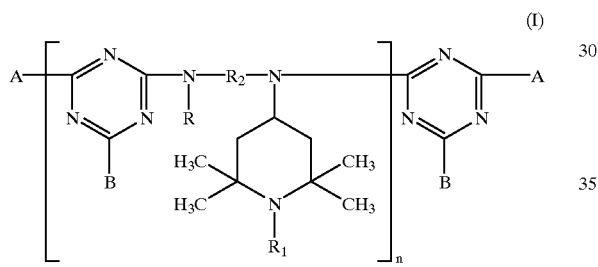

(I)

in which n is 3, 4, 5, 6, 7, 8, 9, 10, 11, 12, 13, 14 or 15;

the radicals $R_1$ are independently of one another hydrogen, $C_1$–$C_8$alkyl, $C_2$–$C_8$hydroxyalkyl, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_{1-12}$alkoxy)carbonyl or having one of the definitions of $R_4$ given below except hydrogen; or $R_2$ is a group of the formula (a), (b) or (c);

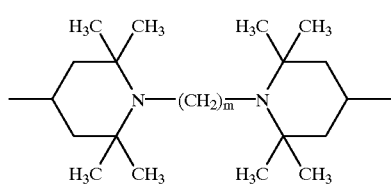

(a)

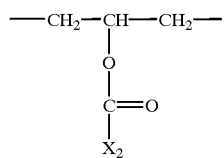

(b)

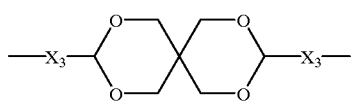

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene; the radicals A are independently of one another —$OR_3$, —$N(R_4)(R_5)$ or a group of the formula (II);

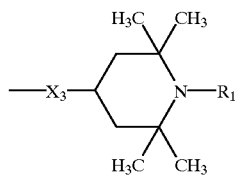

(II)

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

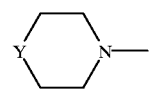

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV),

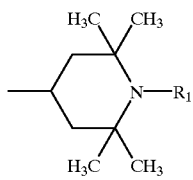

(IV)

or $C_2$–$C_4$alkyl which is substituted in the 2, 3 or 4 position by —OH, $C_1$–$C_8$alkoxy, di($C_1$–$C_4$alkyl) amino or a group of the formula (III);

R has one of the definitions given for $R_6$; and the radicals B have independently of one another one of the definitions given for A;

with the proviso that in the individual recurrent units of the formula (I), each of the radicals B, R, $R_1$ and $R_2$ has the same or a different meaning, and which vary only by the variable n, said mixture having a polydispersity $\overline{M}w/\overline{M}n$ of 1.1 to 1.7;

obtained by 1) reacting a compound of the formula (A)

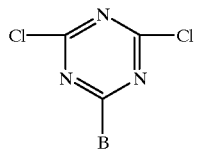

(A)

with a compound of the formula (B)

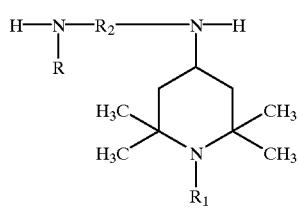

(B)

in a stoichiometric ratio to obtain a compound of the formula (C);

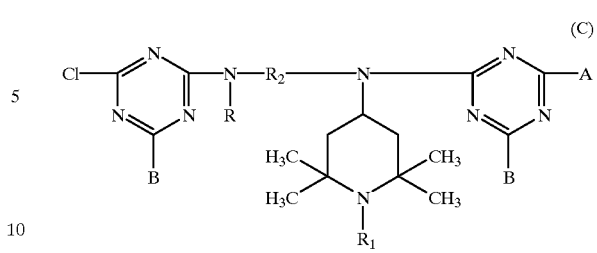

(C)

2) reacting a compound of the formula (C) with a compound of the formula (B) in a ratio of 1:2 to 1:3, to obtain a mixture of at least three different compounds of the formula (D) with n being 3, 4, 5, 6, 7, 8, 9, 10, 11, 12, 13, 14 or 15;

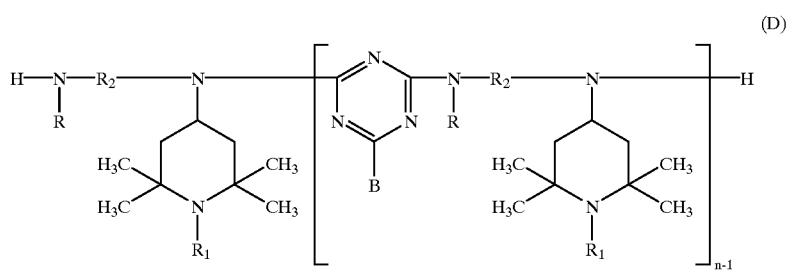

(D)

3) reacting the mixture obtained in 2) with a compound of the formula (E)

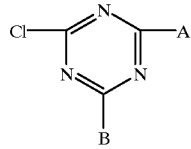

(E)

in a stoichiometric ratio to obtain the mixture; the reactions 1) to 3) being carried out in an organic solvent in the presence of an inorganic base.

28. A mixture according to claim 27, wherein the compound of the formula (E) is a compound of the formula (E*)

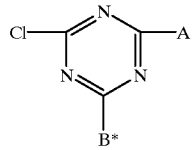

(E*)

wherein B* has one of the definitions given for B; with the proviso that B* is different from B in step 2.

* * * * *

UNITED STATES PATENT AND TRADEMARK OFFICE
CERTIFICATE OF CORRECTION

PATENT NO.      : 6,046,304                                 Page 1 of 2
APPLICATION NO. : 08/756225
DATED           : April 4, 2000
INVENTOR(S)     : Valerio Borzatta et al.

It is certified that error appears in the above-identified patent and that said Letters Patent is hereby corrected as shown below:

Column 2

Lines 25-30, the structure should read:

-- 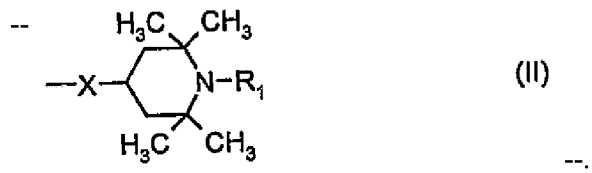 (II)

--.

Column 52

Lines 25-30, the structure should read:

-- 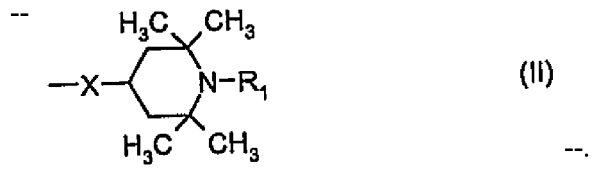 (II)

--.

UNITED STATES PATENT AND TRADEMARK OFFICE
CERTIFICATE OF CORRECTION

PATENT NO.         : 6,046,304
APPLICATION NO. : 08/756225
DATED                  : April 4, 2000
INVENTOR(S)       : Valerio Borzatta et al.

It is certified that error appears in the above-identified patent and that said Letters Patent is hereby corrected as shown below:

Column 62

Lines 30-35, the structure should read:

-- 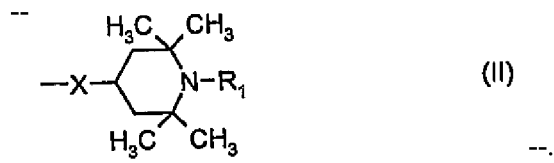  (II)

--.

Signed and Sealed this

Twenty-seventh Day of February, 2007

JON W. DUDAS
*Director of the United States Patent and Trademark Office*